(12) United States Patent
Lei

(10) Patent No.: US 9,675,407 B2
(45) Date of Patent: Jun. 13, 2017

(54) RADIO FREQUENCY TREATMENT APPARATUS

(71) Applicant: Chongqing Peninsula Medical Technology Co., Ltd., Chongqing (CN)

(72) Inventor: Xiaobing Lei, Chongqing (CN)

(73) Assignee: CHONGQING PENINSULA MEDICAL TECHNOLOGY CO., LTD., Chongqing (CN)

(*) Notice: Subject to any disclaimer, the term of this patent is extended or adjusted under 35 U.S.C. 154(b) by 0 days.

(21) Appl. No.: 15/133,194

(22) Filed: Apr. 19, 2016

(65) Prior Publication Data

US 2016/0228178 A1 Aug. 11, 2016

Related U.S. Application Data

(63) Continuation of application No. PCT/CN2015/097434, filed on Dec. 15, 2015.

(30) Foreign Application Priority Data

Dec. 19, 2014 (CN) .......................... 2014 1 0793852
Jan. 21, 2015 (CN) .......................... 2015 1 0030076
Aug. 14, 2015 (CN) .......................... 2015 1 0500549

(51) Int. Cl.
*A61N 1/04* (2006.01)
*A61B 18/14* (2006.01)
(Continued)

(52) U.S. Cl.
CPC ........ *A61B 18/1477* (2013.01); *A61N 1/0476* (2013.01); *A61N 1/06* (2013.01);
(Continued)

(58) Field of Classification Search
CPC ...................... A61B 2018/0016; A61N 1/0476
See application file for complete search history.

(56) References Cited

U.S. PATENT DOCUMENTS 7,115,124 B1* 10/2006 Xiao .................. A61B 18/1477
606/41
2008/0288021 A1* 11/2008 Schmid ..................... A61F 9/08
607/54
(Continued)

FOREIGN PATENT DOCUMENTS

CN          103654949 A    3/2014
CN          104434302 A    3/2015
(Continued)

OTHER PUBLICATIONS

Written Opinion of the International Searching Authority in PCT/CN2015/097434, mailed Mar. 14, 2016.

*Primary Examiner* — Linda Dvorak
*Assistant Examiner* — Yasamin Ekrami
(74) *Attorney, Agent, or Firm* — Syncoda LLC; Feng Ma; Junjie Feng

(57) ABSTRACT

A radio frequency (RF) treatment apparatus includes a main machine and a treatment handpiece. The treatment handpiece may comprise an RF output device, comprising a controller, an RF electrode module, an RF electrode driving circuit, and an RF generation module. The treatment handpiece may also employ a modified arrangement of the plurality of RF electrodes and/or an adjusted series-connection pattern. The treatment handpiece may also be provided with a microneedle member, which includes a plurality of microneedles, a printed circuit board (PCB), and a substrate plate, wherein the plurality of microneedles comprise a plurality of long microneedles and a plurality of short microneedles.

20 Claims, 19 Drawing Sheets

(51) Int. Cl.
    *A61N 1/06*         (2006.01)
    *A61N 1/40*         (2006.01)
    *A61B 18/00*       (2006.01)

(52) U.S. Cl.
    CPC ........ *A61N 1/40* (2013.01); *A61B 2018/0016* (2013.01); *A61B 2018/00083* (2013.01); *A61B 2018/143* (2013.01); *A61B 2018/1467* (2013.01)

(56) References Cited

U.S. PATENT DOCUMENTS

| | | |
|---|---|---|
| 2013/0226269 A1 | 8/2013 | Eckhouse |
| 2015/0366747 A1 | 12/2015 | Lei |
| 2016/0058999 A1* | 3/2016 | Skiba .................. A61N 1/30 607/50 |

FOREIGN PATENT DOCUMENTS

| | | |
|---|---|---|
| CN | 104546122 A | 4/2015 |
| CN | 204446098 U | 7/2015 |
| CN | 105055017 A | 11/2015 |

* cited by examiner

RADIO FREQUENCY TREATMENT APPARATUS

CROSS-REFERENCE TO RELATED APPLICATIONS

The present application is a continuation of, and claims priority to, PCT Application No. PCT/CN2015/097434 filed on Dec. 15, 2015, which in turn claims priority to Chinese Patent Application Nos. CN 201410793852.0 filed on Dec. 19, 2014, CN 201510030076.3 filed on Jan. 21, 2015, and CN 201510500549.1 filed on Aug. 14, 2015. The disclosures of these applications are hereby incorporated by reference in their entirety.

BACKGROUND

As a common type of beauty equipment, a radio frequency (RF) treatment apparatus, sometimes known as an RF beauty device, typically works to facilitate the polar water molecules in skins and subcutaneous tissues to rotate and vibrate at high speeds under the high-frequency, high-power RF field action, allowing rapid heating of tissues to promote subcutaneous fat catabolism and to stimulate the production and restructuring of collagen and elastic fibers, ultimately leading to skin tightening and figure improvement and beautification.

RF treatment by microneedle arrays shows good therapeutic effects on cosmetic fields such as skin beauty, working by generating heat to induce regeneration of collagen, cause injury, shrinkage and necrosis of sebaceous glands to treat acnes, cause injury, shrinkage and necrosis of apocrine sweat glands to treat hyperhidrosis. This technology has been widely used to treat wrinkles, scars, acne, stretch marks, and hyperhidrosis.

The RF electromagnetic wave-mediated skin tightening treatment works by raising the temperature of skin collagen layer to 60-70° C. and keeping the temperature for a short time period to allow the contraction of collagen to achieve skin tightening. Different skin tissues show no selectivity to RF electromagnetic wave, and the energy transfers from the epidermis into the dermis. Because the treatment target tissue is the collagen tissues in the dermal layer, adverse skin reactions on the epidermis layer commonly occur after such treatment, which include flushing, inflammation, and other adverse symptoms.

Currently, the RF beauty devices on the market typically have the weaknesses such as having large deviations of total harmonic power at the nominal load, lack of power impedance feedback, and lack of body temperature detection protection, as well as the unstable power output due to the attenuation of electromagnetic waves during transmission, thus have failed to achieve the desired therapeutic effects.

The Chinese patent CN 103654949B discloses an RF microneedle therapeutic device that effectively overcomes the shortcomings of current RF beauty devices. The device as disclosed herein penetrates deeply under skin to emit radio frequency, which ensures the therapeutic effects on the target tissue, and eliminates the adverse effects associated with the non-selectivity of the RF electromagnetic waves. The disclosures of this patent are hereby incorporated by reference in their entirety.

SUMMARY

An objective of this disclosure is to provide an RF microneedle therapeutic device that ensures the therapeutic effects on the target tissue, and eliminates the adverse effects associated with the non-selectivity of the RF electromagnetic waves.

An objective of this disclosure is to solve the uneven current distribution problems during treatment caused by multiple anodes and cathodes of existing RF beauty devices.

Another objective of this disclosure is to solve the issues including fewer heat concentration regions and poorer uniformity of energy distribution among the RF electrodes in existing RF beauty devices.

Yet another objective is to overcome the difficulties for RF electrode microneedles of existing RF beauty devices to reach target treatment regions.

The disclosure provides an RF microneedle therapeutic device that can effectively protect the skin epidermis. An RF microneedle therapeutic device as disclosed herein may comprise: a main machine, a cable, and a treatment handpiece, wherein: the main machine is connected to the treatment handpiece via the cable; a microneedle transmitter is arranged in the treatment handpiece, wherein at least one driving rod is arranged at front end of the microneedle transmitter and is configured to be driven by a magnetic drive pump disposed in the microneedle transmitter, a reset electromagnet is arranged at back end of the microneedle transmitter and is configured to reset the magnetic drive pump; an RF microneedle treatment unit is arranged at front end of the at least one driving rod, wherein the RF microneedle treatment unit comprises a housing, a base, a plurality of microneedles and at least one spring, wherein the housing is arranged at a frontend opening of the treatment handpiece, the base is arranged in the housing and configured to be driven to move forward by the at least one driving rod, the plurality of microneedles are arranged at a bottom side of, and perpendicular to, the base, the at least one spring is arranged at the bottom side of the base and configured to backwardly reset the base.

In some embodiments, a plurality of microneedles as the RF electrode. The magnetic drive pump disposed in the microneedle transmitter drives the at least one driving rod to move the base in the RF microneedle treatment unit forward to instantly push the microneedles into the dermis or the fat layer, for example 2 mm under skin, which then emit RF for RF treatment. After treatment, the reset electromagnet resets the magnetic drive pump to pull back the at least one driving rod and eliminate the pressure on the base, and the at least one spring helps to move the base and the microneedles back.

The RF microneedle therapeutic device penetrates deeply under skin to emit radio frequency, which ensures the therapeutic effects on the target tissue, and eliminates the adverse effects associated with the non-selectivity of the RF electromagnetic waves. By means of the plurality of microneedles to emit RF in the dermal layer, the epidermis is well protected. This invention can be widely applied to the skin care and beauty treatment of wrinkles, loose skin, scars, scars and hyperhidrosis, and the target tissues can dermis, subcutaneous fat layer, and/or sweat glands.

As the skin tissues are soft tissues, there are difficulties for the microneedles to pierce, and thus the treatment process requires flat pressing of the microneedles against the skin tissues and further requires an instant push of the microneedles into the subcutaneous tissues. The microneedles need to move fast enough to overcome the difficulties in penetrating the skin soft tissues, and the faster the microneedles move, the lower the pain during treatment. Accordingly, the moving speed of the microneedles need to reach 100 mm/s, even 1000 mm/s.

The RF microneedle treatment unit can be mounted in a detachable manner, allowing the microneedles to be dismounted for sterilization and secondary patient use. It has a limit of certain number of uses and is thus a consumable supply.

The RF power supply in the main machine has an output frequency of 0.3 MHz-100 MHz, and can output RF in a continuous manner, a pulsed manner, or a continuous/pulsed mixed manner. The RF treatment can be performed in two modes, a pulsed treatment mode or a continuous treatment mode. The continuous treatment mode typically requires a treatment period of 1-10 s, and a slow heating on skin tissues for treatment, and the temperature of the target region is generally controlled at 40-50° C., to achieve good therapeutic effects without damaging surrounding tissues. The pulsed treatment mode typically completes within 0.1-0.5 s, and because of the short duration of treatment, the skin can tolerate higher temperature. A target region temperature of 60-70° C. can ensure good therapeutic effects by stimulating the regeneration of collagen and promote tightening of fibrous tissues, but if exceeding 75° C., the skin tissues in treatment regions may undergo necrosis. There are differences in the two treatment modes, in the treatment time and the target region temperature.

In the RF treatment, a single-electrode handpiece or a double-electrode handpiece can be used. During treatment using a double-electrode handpiece, the current forms a circuit at the target treatment region, whereas during treatment using a single-electrode handpiece, an additionally attached cathode plate is needed to complete the current circuit.

In a double-electrode handpiece, the electrode arrangement of microneedles can have a variety of ways, and it is typically arranged such that the number of cathodes and the number of anodes are substantially equal, in order to ensure substantially uniform energy distribution at each electrode. Current forms circuits between the cathodes and the anode, and if, for example, two anode and one cathode are present, the cathode carries twice energy as anode, and given the same specification for each microneedle, the energy density of cathode is twice that of anode, causing thus overtreatment.

The RF microneedle treatment unit has an automatic impedance matching functionality. The electromagnetic waves emitted from the main machine are transmitted via the cable to the anodes of the treatment handpiece, and form circuits through the cathodes. The system can detect skin impedance in a short time and correspondingly calculate the power density that is needed, and then output the needed power density. This impedance matching technology ensures that a preset power is output to different patients and on different skin regions under therapy. A control console can also set an alert temperature level to the treatment temperature; in one example, in the pulsed treatment mode, setting the therapeutic output power to be 0.1J and the alert treatment temperature to be 75° C., if the power output is 0.05J and the treatment temperature reaches 75° C., the device stops transmitting radio frequency energy.

A temperature sensor is provided on one of the plurality of microneedles for temperature feedback to ensure safety of treated skin tissues during treatment. If the temperature monitored and fed back by the temperature sensor exceeds the set alert temperature, mandatory stop is triggered to stop emitting radio frequency energy. Depending on the different RF treatment modes, different alarm temperatures are set. In the continuous treatment mode, the alarm temperature can be set in the range of 45-50° C., and set for example, as 50° C.; in the pulsed treatment mode, the alert temperature can be set in the range of 70-75° C., and set for example as 75° C.

The plurality of microneedles can be primarily made of medical-standard stainless steel. Except for the microneedle that is mounted with the temperature sensor, all other microneedles are coated with a gold film, allowing for a good control of impedance change that typically happens on heated metals, which further helps stabilize the output power. Gold has a resistance temperature coefficient of only 56 percent that of stainless steel.

The plurality of microneedles transmits RF only after they pierce into the skin. During treatment, the microneedle body will be in contact with the skin and has different penetration depths, and thus may possibly cause different contact points. In order to avoid the burning on the epidermis caused by RF transmission, the surface of each of the plurality of microneedles is coated with an insulating layer, with only 0.1-1 mm tip of the needles exposed outside the insulating layer.

In order to ensure therapeutic treatment on different parts of the skin, the microneedles need to pierce target tissues, such as the sebaceous glands for the treatment of acne, the sweat glands for the treatment of axillary hyperhidrosis, the dermal tissues for the treatment of skin scar, the fat upper layer for the treatment of cellulite tissues, etc. In this disclosure, the plurality of microneedles has a length range of 4-10 mm; the thickness of needles determines the severity of the lesions, and the finer the needle, the lighter the skin lesions, but also the smaller the range of RF coverage. The plurality of microneedles has a diameter of 0.1-0.3 mm, and preferably set as 0.2 mm.

In a preferred embodiment, each of the array of microneedle has a conical tip, with a diameter of less than 0.03 mm.

At the front end wall of the treatment handpiece, a treatment depth control unit that adjusts how far the base can travel is provided, which is arranged inside the housing of the RF microneedle treatment unit. In this disclosure, an effective length, or substantially the subcutaneous penetration depth, of the plurality of microneedles is 0.5-5 mm and is adjusted by the treatment depth control unit to meet different treatment needs.

There are multiple merits of the RF microneedle therapeutic device as disclosed herein: the device pierces deep into under skin and transmit RF, which ensures the therapeutic effects on the target tissues; only the tips of microneedles can transmit RF energy, which not only provides good protection of the epidermis but also ensures good therapeutic effects; the device is ideal for skin tightening, scar removal, and other facial rejuvenation, and can also be used for treatment of acne and axillary hyperhidrosis, and may also facilitate drug absorption.

Disclosed herein also provides an RF output device, comprising: an RF electrode module, comprising at least one group of RF electrodes; an RF generation module, comprising at least one RF source, wherein the RF generation module is configured to output the at least one RF source, a number of the at least one RF source corresponds to a number of the at least one group of RF electrodes, and the at least one RF source is coupled to the at least one group of RF electrodes through at least one RF electrode driving circuit; a controller, wherein the controller is coupled to the at least one RF electrode driving circuit, and is configured to generate a preset output RF frequency for an excitation source to trigger conduction of the at least one RF electrode driving circuit, so as to drive alternate conduction of the at least one group of RF electrodes and the at least one RF source.

Preferably, the RF electrode driving circuit in the above-mentioned RF output device comprises an optical coupler, a transistor and a relay, wherein a base electrode of the transistor is coupled to the optical coupler through a first resistance, a collector electrode of the transistor is coupled to the relay, and an emitter electrode of the transistor is coupled to an output source.

As a further improvement, an input end of the optical coupler is coupled to one end of a second resistance, another end of the second resistance is coupled to the controller, another input end of the optical coupler is coupled to ground, an output end of the optical coupler is coupled to a power source, another output end of the optical coupler is coupled to one end of the first resistance, another end of the first resistance is coupled to the base electrode of the transistor, the collector electrode of the transistor is coupled to one end of a coil of the relay, another end of the coil of the relay is coupled to the power source, the relay comprises a normally open DPST (double pole single throw) switch and an input end and an output end of the normally open DPST switch is coupled to each of the at least one group of RF electrodes and each of the at least one RF source respectively, the emitter electrode of the transistor is coupled to the ground.

The RF output device as disclosed herein has the following benefit: the configuration of the RF electrode driving circuits to separately drive the conduction of the RF electrode and the RF source and the conduction of the at least one group of RF electrodes to drive the fractional RF treatment can ensure uniform current distribution between each group of RF electrodes. This is a very good solution for the problem of uneven RF current distribution in existing RF treatment.

This disclosure also provides an RF treatment handpiece, aiming to solve the issues including fewer heat concentration regions and poorer uniformity of energy distribution among the RF electrodes in existing RF beauty devices, in order to improve the therapeutic outcomes and cure rates.

RF treatment handpiece may comprise a base and a plurality of electrodes, wherein the plurality of electrodes are mounted on a bottom side of the base, the plurality of electrodes may comprise a plurality of printed circuit nodes or a plurality of RF electrode microneedles, and the plurality of electrodes are arranged in a dot matrix pattern, and more specifically in an M*N matrix, wherein M and N are integers ≥2;

Electrode (i, j) and electrode (i+1, j+1) are series-connected into a branch, where 1≤i≤M−1 and 1≤j≤N−1;

Electrode (M, 1) and electrode (1, N) in a first branch where M and N are odd numbers are parallel-connected with a second branch where i is an odd number to form an electrode in an overall circuit;

Electrode (M, 1) and electrode (1, N) in a third branch where M and N are even numbers are parallel-connected with a fourth branch where i is an even number to form an opposite electrode in the overall circuit;

During treatment using the RF treatment handpiece as disclosed above, the two electrodes of the circuit are wire-connected to the main machine, which provides power supply.

In cases where the plurality of electrodes comprise a plurality of printed circuit nodes, the RF treatment handpiece can be attached to the surface of human skin for non-invasive therapies. In cases where the plurality of electrodes comprise a plurality of RF electrode microneedles, the microneedles of the RF treatment handpiece can pierce into subcutaneous tissues for invasive therapies. Due to the high resistance of human body, circuits form between the anodes and cathodes of the plurality of electrodes, and each individual circuit forms a heat coverage region where heat is dissipated during the current movement in the circuit. The heat can destroy the sweat glands located in the heat coverage region by mechanism of coagulation necrosis. The embodiment of the invention as illustrated in FIG. 9 has a heat coverage area of 24D, twice as that of 12D in the conventional design, and thus can lead to more even energy distribution in FIG. 9 than in FIG. 8.

In order to cure hyperhidrosis, the sweat glands in the whole treatment area need to destroyed by coagulation necrosis, such as a treatment regimen by heating target regions at 55° C.-70° C. and maintaining such for 1-10 s. Alternatively a treatment regimen with increased temperatures and reduced treatment time periods can be applied; in order to achieve the same level of coagulation necrosis, a 10-fold reduction of heating time shall be compensated by a 10° C. increase in temperature, and as such it is necessary to heat target regions at 65° C.-80° C. and maintain such for 0.1 s-1 s. At the same time, due to the large size and high density of apocrine sweat glands, it is ideal to use the RF treatment handpiece with a dot matrix pattern of electrodes, for a more convenient treatment. There are multiple arrangement of the plurality of electrodes, which could be in shape of rectangles, squares, circles, or ovals. The plurality of electrodes may preferentially take a shape of rectangles or squares, for better convenience and improved treatment, and to avoid repeated treatments at target areas.

The RF treatment handpiece as disclosed above may also effectively increase the number of heat concentration regions and distribute heat more evenly by modifying the series-connections between electrodes without changing the arrangement of the electrodes. Thus, it may improve therapeutic effects, increase cure rates, as well as reduce the number of wounds induced by invasive treatment, which allows for timely recovery and reduced recovery time after treatment.

Preferably, any two adjacent electrodes in each row are equally spaced apart, and any two adjacent electrodes in each column are also equally spaced apart.

In the above configuration, the angle formed between the connecting line of any particular electrode with its adjacent anode and the connecting line of the same electrode with its adjacent cathode is 45° or 135°, allowing for more even microcurrent distribution and more heat concentration regions, which in turn improves therapeutic effects and elevates the cure rate.

Where the plurality of electrode employ a plurality of RF electrode microneedles, each of the plurality of RF electrode microneedles takes a cylindrical shape and has a height of 2 mm-5 mm. Each of the plurality of RF electrode microneedles has a tapered tip at a first end far from the base, and has a second end connecting the base, wherein the second end is coated with an insulating layer having a height of 0.3 mm-2 mm.

Because apocrine sweat glands and sweat glands are typically located at 0.5 mm-4.5 mm under skin, whose treatment thus requires that RF microneedles cover more regions than the regions where sweat glands are located. As such, the heat dissipation area for the RF electrode microneedles needs to cover 0.5 mm-5 mm layers under skin, and thus the RF electrode microneedles is set to have a height of 4 mm-5 mm. In order to avoid the thermal damage to epidermis caused by RF electrode microneedles, each of the microneedles has its top end coated with an insulating layer having a height of 0.3 mm-2 mm.

In this disclosure, one of the plurality of RF electrode microneedle may be provided with a blind hole, configured to form in a direction from the base-connecting end to the end with the tapered tip, wherein the bottom of the blind hole is close to the tapered tip and is provided with a temperature sensor, configured to connect to the main machine during use.

Given the need to heat target tissues, as well as the good thermal conductivity of the RF electrode microneedles, the temperature sensor may employ a thermistor, which monitors the change of temperature by changes of the thermal resistance caused by the heat dissipated in the tissues. Different temperatures determine different biological mechanisms in response to the thermal effects. For example, heating at 65° C. for a few seconds can stimulate collagen denaturation and regeneration, and heating at 75° C. for a few seconds can lead to collagen coagulation, whereas heating at 75° C. for 0.1 s can only stimulate collagen denaturation. Levels of thermal resistance fed back by the temperature sensor to the main machine can be used to decide whether or not the RF radiation shall sustain, which allows for better therapeutic effects and avoids possible overtreatment.

In another embodiment of the invention, an RF treatment handpiece may comprise a base and a plurality of electrodes, wherein the plurality of electrodes are mounted on a bottom side of the base, and the plurality of electrodes may comprise a plurality of printed circuit nodes or a plurality of RF electrode microneedles, and may be arranged in a dot matrix pattern, which is characterized by an M*N matrix, wherein M and N are integers ≥2, and all electrodes in at least one row or in at least one column are on a curved line if connected.

All of the electrodes in each column are series-connected to form a branch, and among the series branches, the branches of odd-number columns are connected in parallel to form one electrode in an overall circuit, whereas the branches of even-number columns are connected in parallel to form the opposite electrode in the overall circuit.

During treatment using the RF treatment handpiece as disclosed above, the two electrodes of the circuit are wire-connected to the main machine, which provides power supply. In cases where the plurality of electrodes comprise a plurality of printed circuit nodes, the RF treatment handpiece can be attached to the surface of human skin for non-invasive therapies. In cases where the plurality of electrodes comprise a plurality of RF electrode microneedles, the microneedles of the RF treatment handpiece can pierce into subcutaneous tissues for invasive therapies. Due to the high resistance of human body, circuits form between the anodes and cathodes of the plurality of electrodes, and each individual circuit forms a heat coverage region where heat is dissipated during the current movement in the circuit. The heat can destroy the sweat glands located in the heat coverage region by the mechanism of coagulation necrosis. The RF treatment handpiece as illustrated in FIG. 11 has a heat coverage area of 21D, which is 75% more than that (12D) in the conventional design, and additionally leads to more even energy distribution in FIG. 11 than in FIG. 9.

In order to cure hyperhidrosis, the sweat glands in the whole treatment area need to destroyed by coagulation necrosis, such as a treatment regimen by heating target area at 55° C.-70° C. and maintaining such for 1-10 s. Alternatively a treatment regimen with increased temperatures and reduced treatment time periods can be applied; in order to achieve the same level of coagulation necrosis, a 10-fold reduction of heating time shall be compensated by a 10° C. increase in temperature, and as such it is necessary to heat target area at 65° C.-80° C. and maintain such for 0.1 s-1 s. At the same time, due to the large size and high density of apocrine sweat glands, it is ideal to use the RF treatment handpiece with a dot matrix pattern of electrodes, for a more convenient treatment. There are multiple arrangement of the electrodes, which could be in shape of rectangles, squares, circles, or ovals. The plurality of electrodes may preferentially take a shape of rectangles or squares, for better convenience and improved treatment, and to avoid repeated treatments at target areas.

The RF treatment handpiece as disclosed above may also effectively increase the number of heat concentration regions and distribute heat more evenly by modifying the series connections between electrodes without changing the arrangement of the electrodes. Thus, it may improve therapeutic effects, increase cure rates, as well as reduce the number of wounds induced by invasive treatment, which allows for timely recovery and reduced recovery time after treatment.

Preferably, all electrodes in each of the columns form a straight line whereas all electrodes in each of the rows are not in a straight line.

Preferably, set: the connecting line between any particular electrode and one of its adjacent anode-role electrode as L1, the connecting line between the same electrode and one of its adjacent cathode-role electrode as L2, and the angle formed between L1 and L2 as α, where α is 60° or 120°.

The above configuration allows for more even microcurrent distribution and more heat concentration regions, which in turn improves therapeutic effects and elevates the cure rate.

There are multiple merits of this invention: by adjusting the arrangement of the plurality of electrodes or changing the series connection pattern among the plurality of electrodes, the number of heat concentration regions is increased and the energy distribution is getting more even. These features in turn improve therapeutic effects and increase the cure rate. By employing RF electrode microneedles, the number of wounds can be reduced, which allows for timely recovery after treatment. Through these small improvements, the invention effectively overcomes the shortcomings of conventional configurations and can be widely applied in clinical practice, especially for the treatment of hyperhidrosis and chromhidrosis.

This disclosure also provides a microneedle member and RF microneedle treatment unit comprising the same, in order to overcome the difficulties for microneedles to reach and treat certain target regions of the skin.

The following disclosures are provided herein:

This disclosure provides a microneedle member, comprising a plurality of microneedles, a printed circuit board (PCB) and a substrate plate, wherein the PCB is mounted on the substrate plate, and the plurality of microneedles are mounted on the PCB and are connected with a printed circuit on the PCB to form RF electrodes. The plurality of microneedles may comprise a plurality of long microneedles and a plurality of short microneedles, and the plurality of long microneedles and the plurality of short microneedles are arranged in an array.

Preferably, the length of the plurality of long microneedles is 0.1 mm-5.0 mm longer than that of the plurality of short microneedles.

Preferably, the bottom end of each of the plurality of long microneedles and each of the plurality of short microneedles is coated with an insulating layer.

Preferably, the insulating layer has a height of 0.1 mm-2.5 mm.

Preferably, the top end of each of the plurality of long microneedles is coated with a second insulating layer.

Preferably, the plurality of long microneedles constitute the anode/cathode of the RF electrodes, and the plurality of short microneedles constitute the cathode/anode of the RF electrodes.

Preferably, a temperature sensor is disposed in one of the plurality of microneedles, and the temperature sensor has a response time of 10 ms-200 ms.

This disclosure also provides an RF microneedle treatment unit, comprising a housing and a motor, wherein the housing is provided with a cavity, a front end of the housing is provided with a plurality of microneedle through-holes which connect the cavity, a rear end of the housing is provided with a plurality of microneedle bullet-holes. The RF microneedle treatment unit also comprises the microneedle member as disclosed above. The microneedle member is fittingly arranged between the plurality of microneedle through-holes and the plurality of microneedle bullet-holes through an elastic member, and the plurality of microneedles in the microneedle member are configured to be pushed by a driving rod of the motor to move out of the plurality of microneedle through-holes through the plurality of microneedle bullet-holes.

Preferably, a temperature sensor is disposed in one of the plurality of microneedles.

Compared with the prior art, the present invention, by modifying the microneedle member to comprise both a plurality of long microneedles and a plurality of short microneedles without modifying other existing components, conveniently overcomes the difficulties for microneedles to reach target regions, and achieves a greater therapeutic effect through further improvements on the plurality of long microneedles and the plurality of short microneedles.

The structure, scale, size, etc. of attached drawings in this specification are only used to reveal the contents disclosed herein and to facilitate the understanding and reading by those familiar with the technology, but are not restrictive to how this invention is implemented. Thus any structural modifications, proportional adjustments, or size changes, so long as they do not affect the functionalities and purpose of this invention, shall remain in the scope of this disclosure. At the same time, the terms referenced in this disclosure, such as "front", "back", "vertical", "horizontal", "top", "bottom", "inside", and "outside", "up", "down", "left", "right", "middle" and "a" and other terms, are also used for disclosure description and description simplification only, rather than indicate or imply the device and elements are required to have specified directions, or structured and operate in a specified direction. Therefore, it can't be taken as limitation on this disclosure. The following pairs of terms used in this disclosure, such as "positive electrode" and anode, and "negative electrode" and cathode, are interchangeable.

Otherwise specified and limited, terms used in this disclosure description, such as "connected" and "connection" are with a broad meaning. For example, it could be mechanical or electrical connection, or two inner elements connection; it could be direct correction or connected by a media. For normal technicians in this field, they are allowed to acquire the exact meaning of above terms based on actual conditions.

Other embodiments and implementations may become apparent in view of the following descriptions and the attached drawings

BRIEF DESCRIPTION OF DRAWINGS

To more clearly illustrate the embodiments of the disclosure, the following is a brief description of the drawings, which are for illustrative purpose only. For those of ordinary skills in the art, other drawings of other embodiments can become apparent based on these drawings.

FIG. 3A is a structure diagram of an RF electrode array;

FIG. 3B is an under-current diagram of the RF electrode array;

FIG. 3C is a structure diagram of another RF electrode array;

FIG. 3D is an under-current diagram of the RF electrode array;

DETAILED DESCRIPTION

Figure 1B:
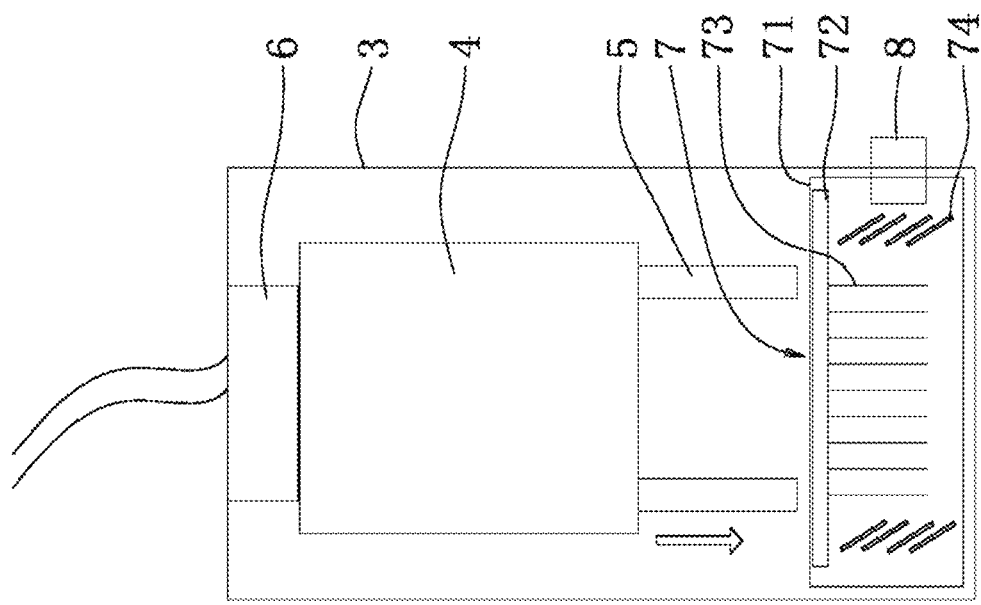
FIG. 1B illustrates an inside configuration of a treatment handpiece of the RF microneedle therapeutic device.

In the following, with reference to the drawings of various embodiments disclosed herein, the technical solutions of the embodiments of the disclosure will be described in a clear and fully understandable way. It is obvious that the described embodiments are merely a portion but not all of the embodiments of the disclosure. Based on the described embodiments of the disclosure, those ordinarily skilled in the art can obtain other embodiment(s), which come(s) within the scope sought for protection by the disclosure.

In an aspect, a radio frequency (RF) treatment apparatus is provided, comprising a main machine and a treatment handpiece, wherein: the main machine comprises a power supply disposed therein and is coupled to the treatment handpiece via a cable; and the treatment handpiece comprises an RF output device, the RF output device comprising a plurality of RF electrodes.

In some embodiments, the RF output device comprises: an RF electrode module, comprising at least one group of RF electrodes; an RF generation module, comprising and configured to output at least one RF source, wherein a number of the at least one RF source corresponds to a number of the at least one group of RF electrodes, and the at least one RF source is coupled to the at least one group of RF electrodes through at least one RF electrode driving circuit; and a controller, wherein the controller is coupled to the at least one RF electrode driving circuit, and is configured to generate a preset output RF frequency for an excitation source to trigger conduction of the at least one RF electrode driving circuit, so as to drive alternate conduction of the at least one group of RF electrodes and the at least one RF source.

In some embodiments, each of the at least one RF electrode driving circuit comprises an optical coupler, a transistor, and a relay, wherein: a base electrode of the transistor is coupled to the optical coupler via a first resistance; a collector electrode of the transistor is coupled to the relay; and an emitter electrode of the transistor is coupled to an output source.

In some embodiments, an input end of the optical coupler is coupled to one end of a second resistance; another end of the second resistance is coupled to the controller; another input end of the optical coupler is coupled to ground; an output end of the optical coupler is coupled to a power source; another output end of the optical coupler is coupled to one end of the first resistance; another end of the first resistance is coupled to the base electrode of the transistor; the collector electrode of the transistor is coupled to one end of a coil of the relay; another end of the coil of the relay is coupled to the power source; the relay comprises a normally open end and a normally close end, coupled to one of the at least one group of RF electrodes and one of the at least one RF source, respectively; and the emitter electrode of the transistor is coupled to the ground.

In some embodiments, another end of the second resistance is coupled with an excitation source.

In some embodiments, the transistor is an NPN transistor.

In some embodiments, each of the at least one group of RF electrodes comprises an RF anode and an RF cathode, or comprises an RF electrode array, the RF electrode array comprising a plurality of RF anodes and a plurality of RF cathodes.

In some embodiments, in the treatment handpiece, the plurality of RF electrodes comprise a plurality of RF electrode microneedles, wherein: each of the plurality of RF electrode microneedles takes a cylindrical shape and has a height of 2 mm-5 mm; and each of the plurality of RF electrode microneedles has a tapered tip at a first end far from the base, and has a second end connecting the base, wherein the second end is coated with an insulating layer having a height of 0.3 mm-2 mm.

In some embodiments, one of the plurality of RF electrode microneedles is provided with a blind hole, wherein: the blind hole is configured to form in a direction from the second end to the first end of the one of the plurality of RF electrode microneedles; a bottom of the blind hole is configured to be close to the tapered tip of the one of the plurality of RF electrode microneedles; and a temperature sensor is arranged at the bottom of the blind hole.

In some embodiments, the treatment handpiece further comprises an RF microneedle treatment unit, the RF microneedle treatment unit comprising a microneedle member, wherein the microneedle member comprises: a plurality of microneedles; a printed circuit board (PCB); and a substrate plate, wherein: the PCB is mounted on the substrate plate; the plurality of microneedles are mounted on the PCB and are coupled to a printed circuit on the PCB to form a plurality of RF electrodes, wherein: the plurality of microneedles comprise a plurality of long microneedles and a plurality of short microneedles, and the plurality of long microneedles and the plurality of short microneedles are arranged in an array.

In some embodiments, length of the plurality of long microneedles is 0.1 mm-5.0 mm longer than length of the plurality of short microneedles.

In some embodiments, a bottom end of each of the plurality of long microneedles and each of the plurality of short microneedles is coated with an insulating layer.

In some embodiments, the insulating layer has a height of 0.1 mm-2.5 mm.

In some embodiments, a top end of each of the plurality of long microneedles is further coated with a second insulating layer.

In some embodiments, the plurality of long microneedles constitute an anode of the RF electrodes and the plurality of short microneedles constitute a cathode of the RF electrodes; or the plurality of long microneedles constitute a cathode of the RF electrodes and the plurality of short microneedles constitute an anode of the RF electrodes.

In some embodiments, a temperature sensor is arranged in one of the plurality of microneedles.

In some embodiments, the temperature sensor has a response time of 10 ms-200 ms.

In some embodiments, the temperature sensor has a response time of 100 ms.

In some embodiments, the RF microneedle treatment unit further comprises a housing and a motor, wherein: the housing is provided with a cavity; a front end of the housing is provided with a plurality of microneedle through-holes, wherein the plurality of microneedle through-holes connect the cavity; a rear end of the housing is provided with a plurality of microneedle bullet-holes; the microneedle member is fittingly arranged between the plurality of microneedle through-holes and the plurality of microneedle bullet-holes through an elastic member; and the plurality of microneedles in the microneedle member are configured to be pushed by at least one driving rod of the motor to move out of the plurality of microneedle through-holes through the plurality of microneedle bullet-holes.

In some embodiments, the elastic member comprises at least one spring.

In some embodiments, a temperature sensor is arranged in one of the plurality of microneedles.

Some embodiments effectively solve at least some of the problems of existing RF treatment technologies, including uneven current distribution, fewer heat concentration regions and poorer uniformity of energy distribution among the RF electrodes, and the difficulties for RF electrode microneedles to reach target treatment regions.

Figure 1A:
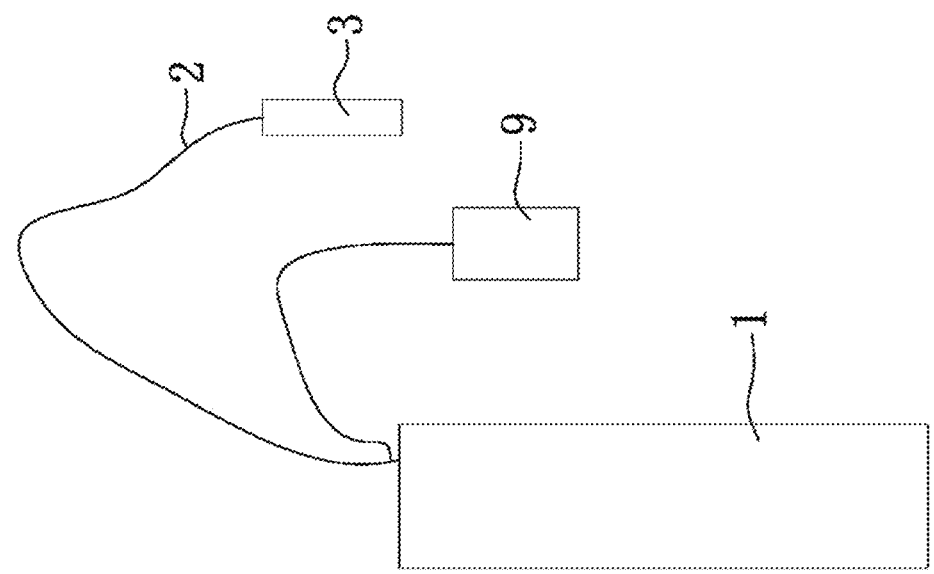
FIG. 1A is a schematic diagram of an RF microneedle therapeutic device.

FIG. 1A illustrates a schematic diagram of an RF microneedle therapeutic device; FIG. 1B illustrates an inside configuration of a treatment handpiece of the RF microneedle therapeutic device. As shown in FIGS. 1A and 1B, an RF power supply and a control circuit coupled to the RF power supply are arranged inside the main machine 1. The RF power supply has an output frequency of 0.3 MHz-100 MHz, and can output RF in a continuous manner, a pulsed manner, or a continuous/pulsed mixed manner. The top end of the main machine 1 is connected to the tail end of the treatment handpiece 3 via the cable 2.

The treatment handpiece 3 has a closed back end and has an opening at the front end. A microneedle transmitter 4 is arranged in the treatment handpiece 3, wherein at least one driving rod 5 is arranged at a front end of the microneedle transmitter 4 and is configured to be driven to move at a speed of more than 100 mm/s by a magnetic drive pump disposed inside the microneedle transmitter 4. A reset electromagnet 6 configured to reset the magnetic drive pump is arranged at a back end of the microneedle transmitter 4 and inside the treatment handpiece 3. Both the reset electromagnet 6 and the microneedle transmitter 4 are wire-connected to the control circuit in the main machine 1. The mechanism by which the reset electromagnet 6 controls the magnetic drive pump is well known and not detailed herein.

As shown in FIGS. 1A and 1B, an RF microneedle treatment unit 7 is arranged at a front end of the at least one driving rod 5 and is disposed in the front end opening of the treatment handpiece 3. The RF microneedle treatment unit 7 comprises a housing 71, a base 72, a plurality of microneedles 73 and at least one spring 74, wherein the housing 71 has an opening at a front end and is mounted in the treatment handpiece 3 in a detachable manner, the base 72 is arranged, and configured to slide, in the housing 71, and is configured to be driven to move forward by the at least one driving rod 5. A plurality of microneedles 73 is arranged on a bottom side of the base 72, and is connected to the RF power supply in the main machine via the control circuit. The plurality of microneedles 73 can be arranged to be 10×10 and have a total of 100 microneedles, to be 7×7 and have a total of 49 microneedles, or to be 10×5 and have a total of 50 microneedles. The number of microneedles and the manner for arrangement rely on real needs. Each of the plurality of microneedles 73 is perpendicular to the base 72.

As shown in FIG. 1B, the plurality of microneedles 73 is primarily made of medical-standard stainless steel. One of the array of microneedle 73 is mounted with a temperature sensor, configured to feedback temperature to ensure safety of treated skin tissues during treatment. All other microneedles are coated with a gold dielectric film, allowing for a good control of impedance change that typically happens on heated metals, which further helps stabilize the output power. Each of the plurality of microneedles 73 is coated with an insulating layer, with only 0.1-1 mm tip of the microneedles exposed outside the insulating layer. By contacting skin with the insulating layer of the plurality of microneedles 73, burning on the epidermis caused by RF transmission can be effectively avoided. The plurality of microneedles 73 has a length of 4-10 mm and a diameter of 0.1-0.3 mm. Each of the array of microneedle 73 has a conical tip, with a diameter of less than 0.03 mm. A treatment depth control unit 8 is arranged at a frontend wall of the treatment handpiece 3 to define how far the base 72 can travel, which is arranged inside the housing 71 of the RF microneedle treatment unit 7. The treatment depth control unit 8 is configured to move back and forth to adjust the effective treatment length, or substantially the subcutaneous penetration depth, of the plurality of microneedles 73 to be 0.5-5 mm.

The treatment handpiece 3 can be a double-electrode handpiece, wherein part of the plurality of microneedles serve as anodes and part as cathodes, and the number of cathodes and the number of anodes are substantially equal.

The treatment handpiece 3 can be a single-electrode handpiece, wherein substantially all of the plurality of microneedles are anodes, and the treatment handpiece additionally requires a cathode plate 9, which is wire-connected with the control circuit in the main machine 1.

The working mechanism of the device is as follows: 1) Apply skin anesthesia; 2) Set the output power and the alert temperature on the device controller, such as an output power of 0.1J and an alert temperature of 70° C.; 3) Adjust the treatment depth by manipulating the treatment depth control unit 8 on the treatment handpiece 3. For example, de-wrinkling treatment requires a setting of treatment depth of 1.5 mm; 4) Control the microneedle transmitter 4 to drive the magnetic drive pump to move forward the at least one driving rod 5, which in turn pushes the base 71 in the RF microneedle treatment unit 7 forward and instantly push the plurality of microneedles 73 into the skin (it takes about 0.01 s) where the plurality of microneedles 73 emits RF energy (duration time depends on whether a pulsed treatment mode or a continuous treatment mode is applied). Then the reset electromagnet 6 resets the magnetic drive pump to pull back the at least one driving rod 5 back to the original position, and the base 71 and the plurality of microneedles 73 are reset to move back under the action of the at least one spring 74; and 5) Repeat step 4 for treatment of a different target skin region.

Figure 2:
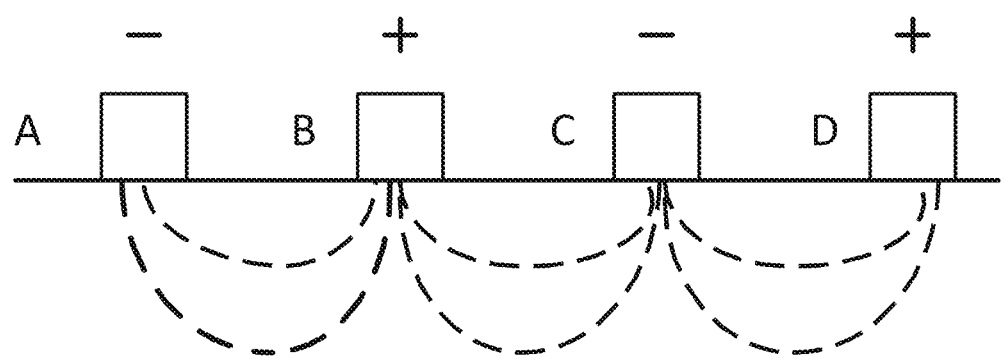
FIG. 2 is an electric effect schematic diagram of a conventional frictional RF therapy apparatus with an existing arrangement of RF electrode structure.

Existing Fractional RF therapy technology treats skin by allowing the positive and negative RF electrodes to conduct through the skin tissue. Typically the RF electrodes on a conventional therapeutic apparatus are based on an array. FIG. 2 illustrates an electric effect schematic diagram of a conventional frictional RF therapy apparatus with an existing arrangement of RF electrode structure. This figure also marks out the current flow distribution between RF electrodes. Because the electric charge moves along the direction of least resistance, as for negative electrode A and positive electrode D, due to the presence of opposite electrode B or C, the current flows from electrode A to B not D. In addition, electrode B provides current path to both electrode C and electrode A at the same time, so the current passing through B is an overlap of current passing electrode A and electrode C.

As such, during treatment energy is calculated by the energy formula: $Q=I^2*R*t$, where I is the current, R the skin impedance (as resistance), t the time period for the passing current. Setting the positive electrode B and D by the method of potential, and setting the current as I, then the current at electrode A is 0.5I, the current at electrode C is 1.5I.

Figures 3A, 3B, 3C, 3D:
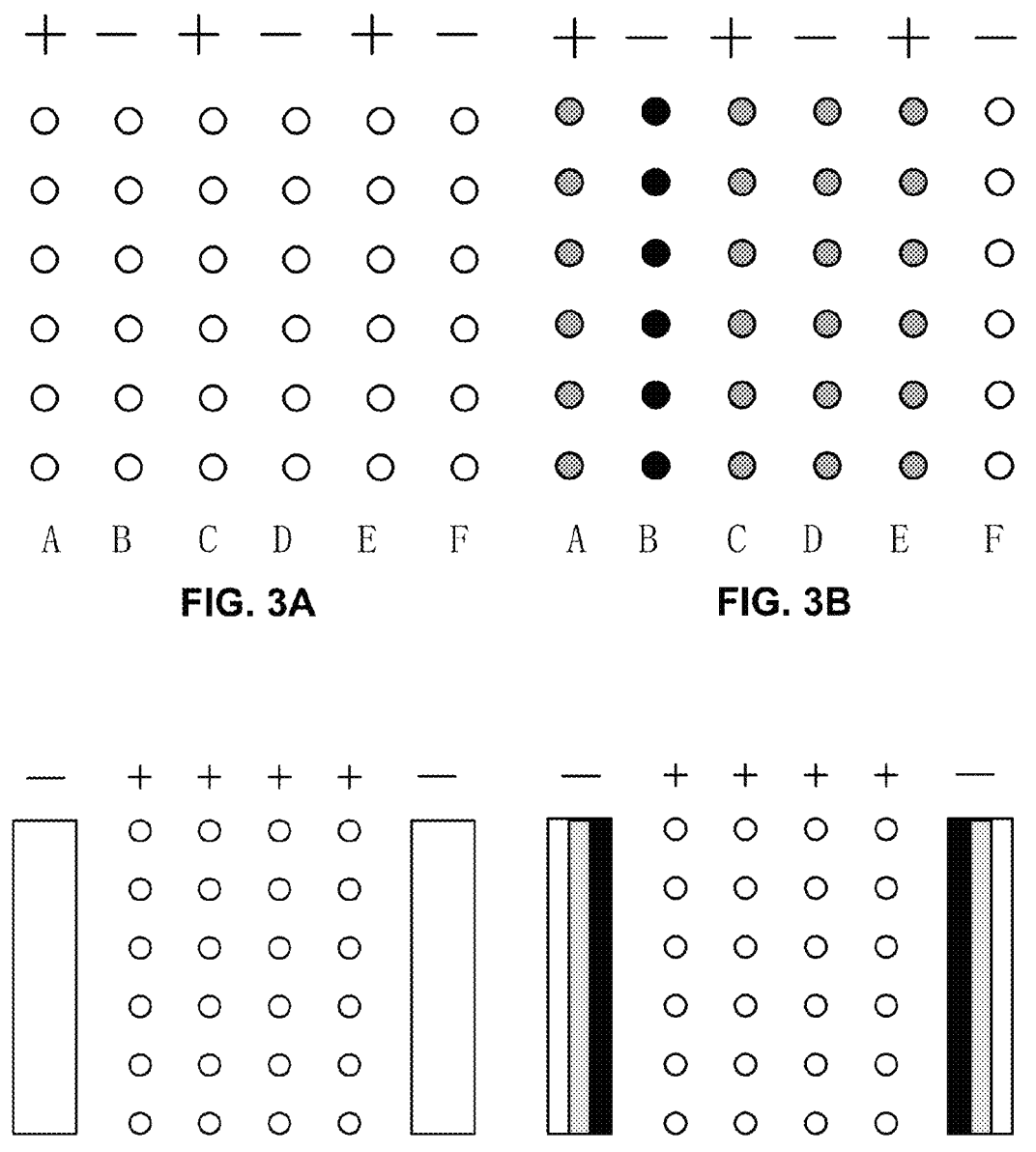

In addition, several configurations of existing RF electrode arrays in conventional frictional RF therapy apparatuses are also described, which all apply a same circuit structure as above, with a change only on the RF electrode arrangement. FIG. 3A illustrates the structure diagram of an existing RF electrode array, wherein both the positive electrodes and the negative electrodes are arranged as matrices. Setting the current at positive electrodes as I (namely the current at electrode A, C and E is I), the current at electrode B is 1.5I, the current at electrode D is I, the current at electrode F is 0.5 I. Thus during use of the apparatus, the current density at electrode B is 3 times that at electrode F, and 1.5 times that at electrode A/C/D/E (FIG. 3B).

Furthermore, as shown in FIG. 3C, which illustrates the structure diagram of another existing RF electrode array, where all the dot-like electrodes in the middle are positive electrodes, all the long strip-like electrodes at the edge are negative electrode. The corresponding current and heating diagram of the RF electrode array is shown in FIG. 3D. As shown in FIG. 3D, the energy distribution on the middle positive RF electrodes is relatively uniform, but the energy distribution is tilted at the edge negative RF electrodes.

Taken together, there is a significant difference in the treatment energy of existing RF electrode arrays during treatment, resulting in uneven treatment doses.

Implementation Example 1

Figure 4A:
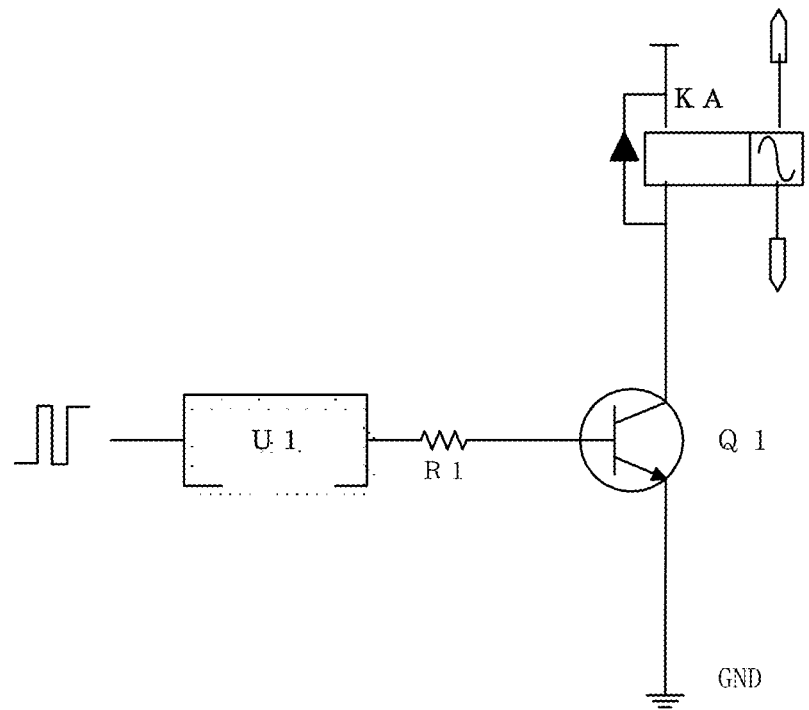
FIG. 4A illustrates the working principle of an RF electrode according to some embodiments.

In order to solve the abovementioned problems, the disclosure provides an RF electrode driving circuit. FIG. 4A illustrates the working principle of an RF electrode driving circuit diagram according to some embodiments of the disclosure. The RF electrode driving circuit comprises an optical coupler U1, a transistor Q1 and a relay KA, wherein a base electrode of the transistor Q1 is coupled to the optical coupler U1 through a resistance R1, a collector electrode of the transistor Q1 is coupled to the relay KA, and an emitter electrode of the transistor Q1 is coupled to the output source.

In the RF electrode driving circuit, an input end of the optical coupler U1 is configured to receive an excitation source (for example, the high level) in order to trigger the conduction between the collector electrode and the emitter electrode of the transistor Q1, thus causing a coil of the relay to attach to a normally open end so as to drive the switch to close or shut off.

Figure 4B:
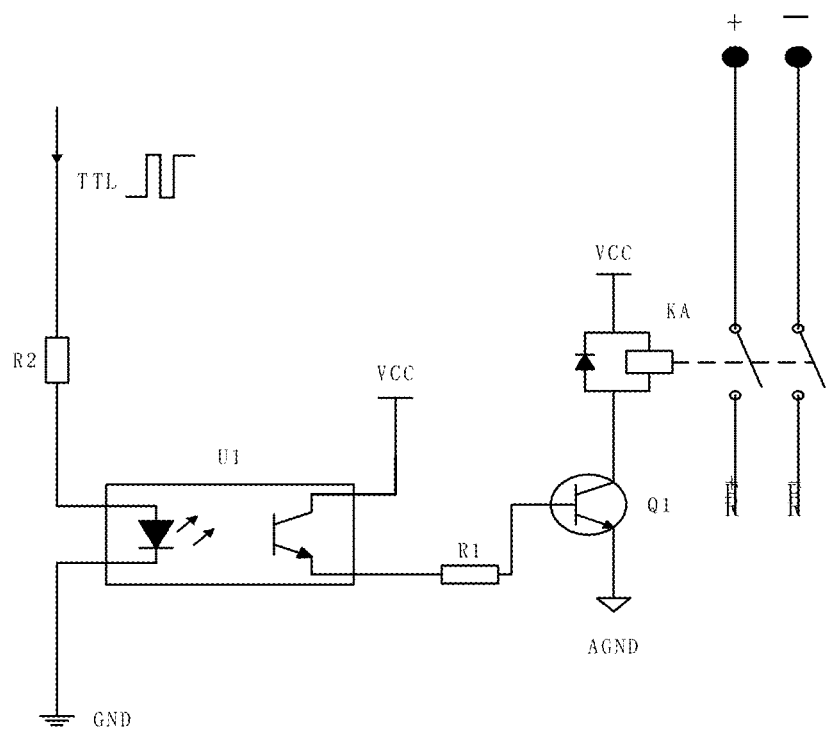
FIG. 4B is a driving circuit diagram of the RF electrode.

Specifically, FIG. 4B illustrates the circuit diagram of the RF electrode driving circuit in FIG. 4A, where an anode of an input end of the optical coupler U1 is coupled to a resistance R2, a cathode of the input end of the optical coupler U1 is coupled to the ground, one output end of the optical coupler U1 is coupled to a power source VCC, another end of the optical coupler U1 is coupled to one end of the resistance R1; another end of the resistance R1 is coupled to the base electrode of the transistor Q1; the collector electrode of the transistor Q1 is coupled to one end of the coil of the relay KA, another end of the coil of the relay KA is coupled to the power source VCC, and the emitter electrode of the transistor Q1 is coupled to the output source (or equipotential).

In practice, the RF electrode driving circuit can be mounted between an RF source and an RF electrode, to drive the RF electrode and the RF source for conduction or disconnection. Among them, the resistance R2 can limit the current; connection or arrival of the excitation source causes conduction of the optical coupler, an increase of current in the resistance R1, which in turn increases voltage in the base electrode of the transistor and causes conduction of the transistor, then the coil of the relay have electricity and attaches to the normally open end, so as to make conduction of the RF electrode with the RF source. The optical coupler is configured to prevent any effects accidentally caused by the RF electrode or the RF source on the excitation source, so as to guarantee the safety of the circuit.

The RF electrodes can also be driven to work directly by the relay and transistor, only that it lacks certain safety. In addition, the transistor can be NPN, and connection between the transistor and the optical coupler and the relay, if not disclosed herein, can be a commonly known approach by those skilled in the art, and no details are provided herein.

Implementation Example 2

Furthermore, the RF electrode driving circuit 520 can be designed to have an RF electrode array different from existing RF electrode arrays, and in the RF electrode array, the electric current can be maintained as uniform, which can prevent uneven current distribution.

Figure 5:
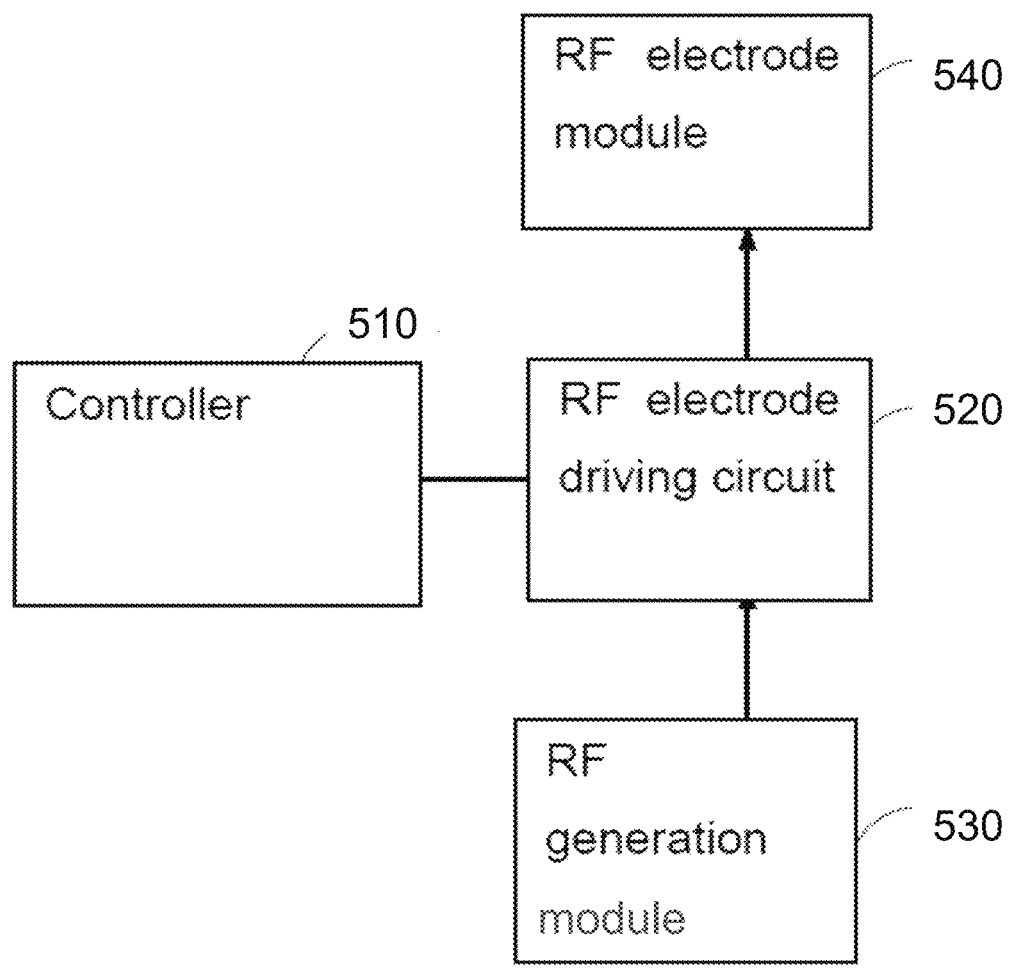
FIG. 5 illustrates the working principle of an RF output device according to some embodiments.

Specifically, FIG. 5 illustrates the working principle of an RF output device according to some embodiments. The RF output device comprises: an RF electrode module 540, comprising at least one group of RF electrodes; an RF generation module 530, configured to output at least one RF source, wherein a number of the at least one RF source corresponds to a number of the at least one group of RF electrodes, and the at least one RF source is coupled to the at least one group of RF electrodes through at least one RF electrode driving circuit 520; a controller 510, wherein the controller is coupled to the at least one RF electrode driving circuit 520, and is configured to generate a preset output RF frequency for an excitation source to trigger conduction of the at least one RF electrode driving circuit 520, so as to drive alternate conduction of the at least one group of RF electrodes and the at least one RF source.

Specifically, each of the at least one group of RF electrodes in the RF electrode module 540 can be arranged in a regular dot matrix, and each of the at least one group of RF electrodes comprises an RF anode and an RF cathode, which are respectively coupled to one end of a double pole single throw (DPST) switch of the relay in the RF electrodes driving circuit 520. The number of the at least one group of RF electrodes match with the number of the at least one RF electrode driving circuit 520. Correspondingly, each of the at least one RF sources is coupled to another end of the DPST switch of the relay in the RF electrode driving circuit 520.

Specifically, the controller 510 can be a single-chip microcomputer, which is configured to generate a preset output RF frequency for an excitation source to trigger alternate conduction of the at least one RF electrode driving circuit 520, which in turn triggers conduction between the at least one RF source and the at least one group of RF electrodes, which are both coupled to the at least one RF electrode driving circuit 520.

Figure 6A:
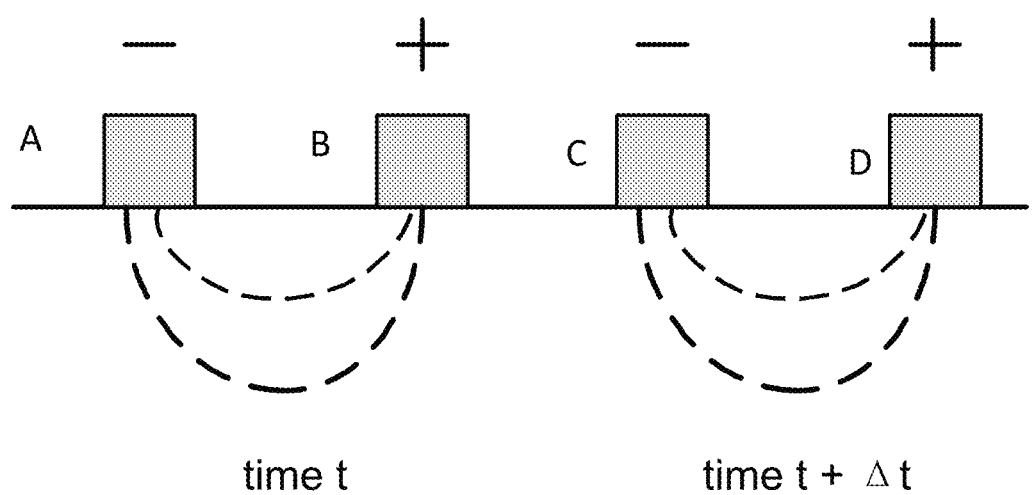
FIG. 6A illustrates the actual effect (A) of an RF output device with two groups of RF electrodes.
Figure 6B:
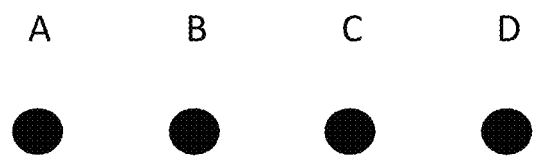
FIG. 6B illustrates the current distribution effect of the RF output device.

For example, FIGS. 6A and 6B illustrate the actual effect and the current distribution of an RF output device with two groups of RF electrodes, respectively. As shown, A and B are a group of RF electrodes, C and D a group of RF electrode. During treatment, according to the excitation frequency, at time t, RF electrodes A and B connects the anode and the cathode of an RF source at the same time, at time t+Δt, RF electrodes C and D connects the anode and the cathode of the RF source at the same time (as shown in FIG. 6A). Thus if the current size is I, then the current flowing through electrode ABCD are equal (as shown in FIG. 6B), which achieves the purpose of uniform treatment by having an even dose and little side effect.

Furthermore, because normally we need to treat the whole surface quickly, launch time for one specific RF anode/cathode group is controlled within 0.5 s, and more specifically within 0.2 s-0.3 s.

Figure 7A:
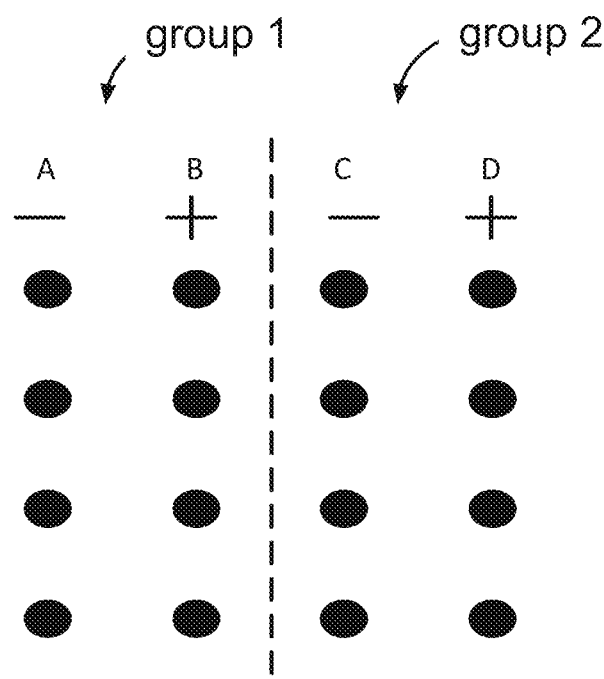
FIG. 7A illustrates a square RF electrode arrangement diagram according to some embodiments.

Furthermore, the one group of RF electrodes can be expanded to comprise one or multiple RF electrode arrays, thus forming various arrangements of RF electrode in the RF electrode module 540. FIG. 7A shows a square RF electrode arrangement diagram, which includes 2 groups of RF electrodes: group1 and group1 2. In actual treatment, group 1 and group 2 are triggered to work alternately, which not only satisfies the purpose of quick treatment for a large-area target region, but also ensures an equal current size for each of the group of RF electrodes.

Figure 7B:
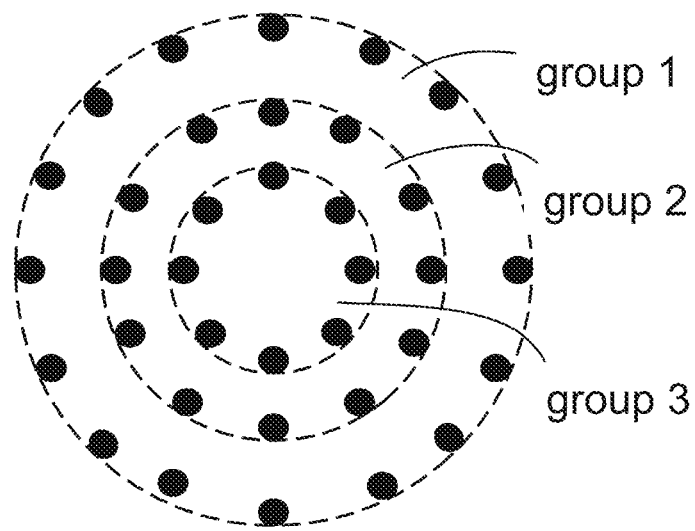
FIG. 7B illustrates a circle RF electrode arrangement diagram according to some embodiments of the disclosure.

FIG. 7B shows a round RF arrangement diagram, which includes three groups of RF electrodes: group 1, group 2 and group 3. In the actual treatment, group 1, group 2 and group 3 work in an alternate way, which also not only satisfies the purpose of quick treatment for a large-area target region, but also ensures an equal current size for each of the group of RF electrodes.

In summary, the configuration of the RF electrode driving circuits 520 to separately drive the conduction of the RF electrode and the RF source and the alternate conduction of the at least one group of RF electrodes to drive the fractional RF treatment can ensure uniform current distribution between each group of RF electrodes. Therefore, this disclosure effectively overcomes the shortcoming in the existing technology and has high industrial value.

Figure 8:
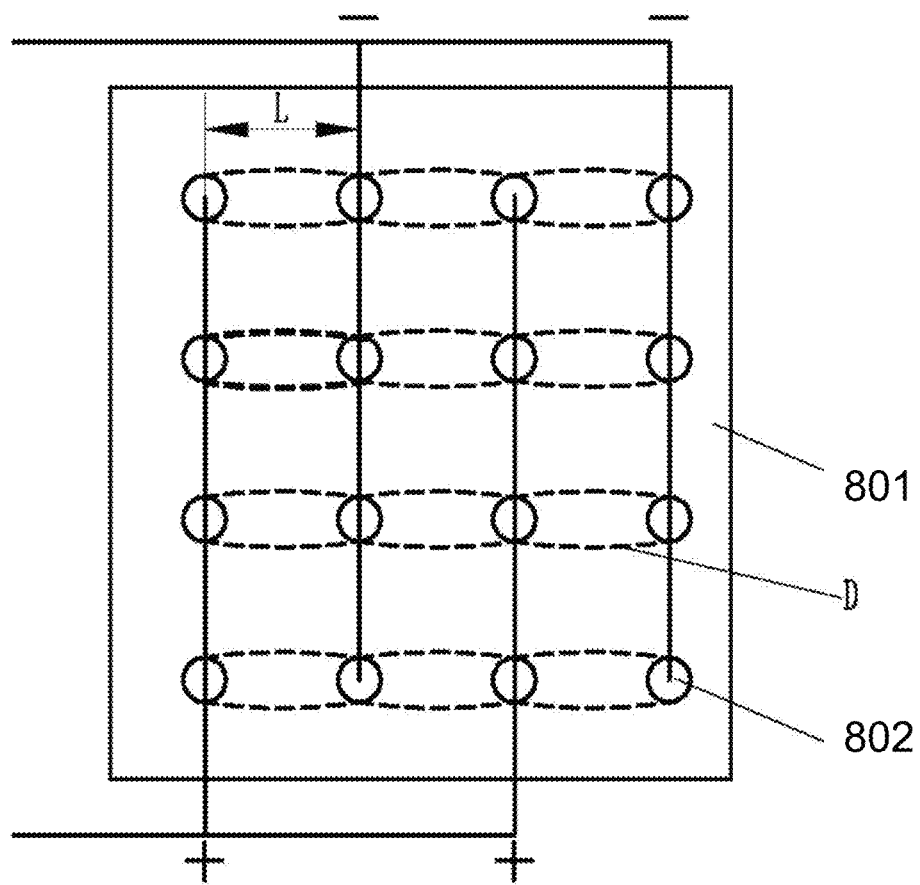
FIG. 8 illustrates the schematic structural diagram of a conventional RF treatment handpiece.

There is a conventional RF treatment handpiece, which in combination with other parts such as the main machine, can be applied for both invasive and non-invasive therapy. As shown in FIG. 8, the conventional RF treatment handpiece comprises a base 801, wherein at least one electrode 802 is arranged on the bottom side of the base. The at least one electrode 802 may be at least one printed circuit node, used for a non-invasive therapy, or at least one RF electrode microneedle, used for an invasive therapy. The at least one electrode 802 is arranged in an array, and may form an M*N matrix. In the matrix, each pair of the adjacent electrodes 802 have same distances; all electrodes 802 in each column are series-connected; all the electrodes 802 in odd number columns are connected in parallel to form one electrode of the overall circuit, and all the electrodes 802 in even number columns are connected in parallel to form the opposite electrode of the overall circuit. The treatment handpiece as shown in FIG. 8 comprises two groups of anodes and two groups of cathodes, which together form an electrode array; an anode array and a cathode array that are adjacent to each other form a current circuit to heat the target region in skin which is covered by the current circuit. Set the current circuit region formed between an anode array and a cathode array which defines the heat concentration area as D, and the conventional treatment handpiece as shown in FIG. 8 has 12D.

The conventional RF treatment handpiece as illustrated in FIG. 8 has the following disadvantages: arrangement of the array of electrodes 802 as shown above results in few heat concentration regions and poor uniformity, which may lead to poor therapeutic effects and low cure rates. To improve the therapeutic effects and the cure rates, the number of electrodes 802 can be increased and the distance between adjacent electrodes 802 can be narrowed. Despite these improvements, however, the array of electrodes 802, where comprising RF electrode microneedles, may lead to increased number of wounds, resulting in longer recovery after treatment.

Embodiment 1

Figure 9:
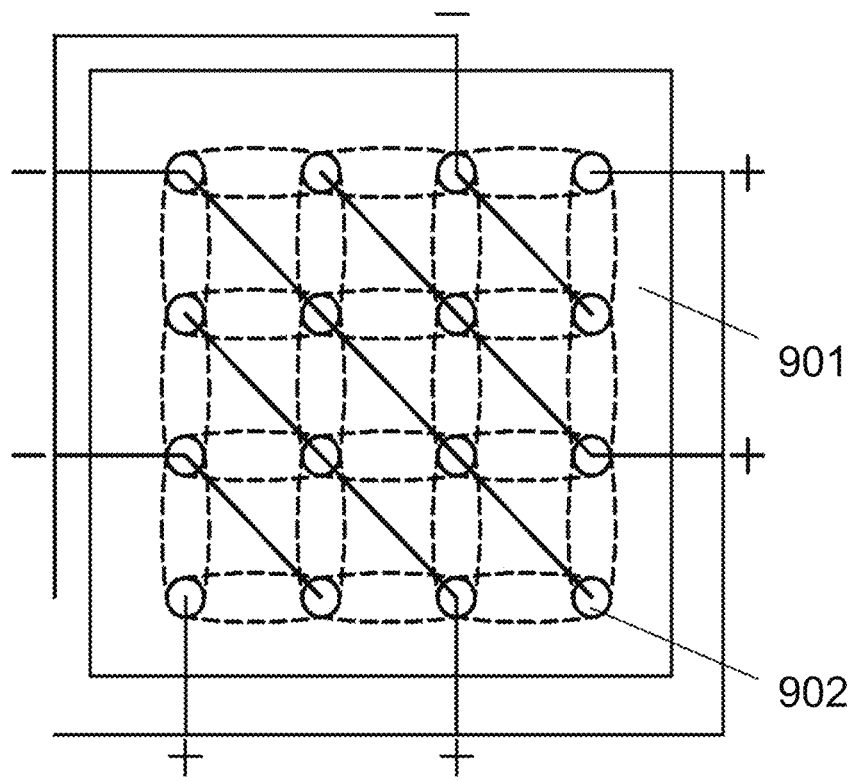
FIG. 9 illustrates a schematic diagram of an RF treatment handpiece according to Embodiment 1 of this invention.
Figure 10:
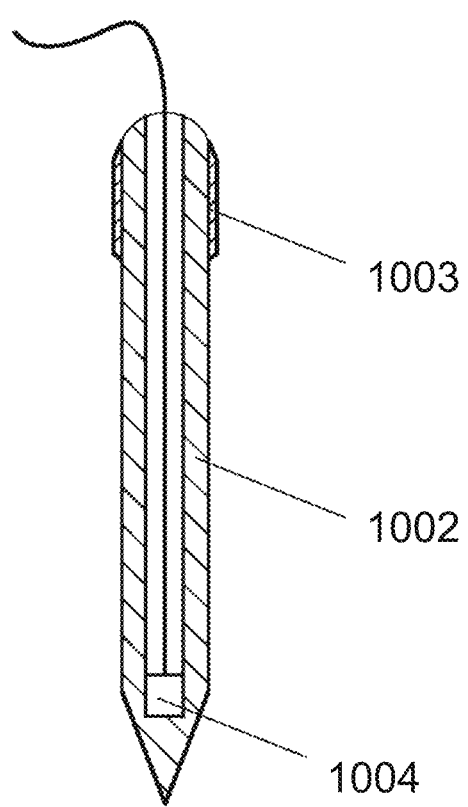
FIG. 10 is a schematic diagram of a RF electrode microneedle employed in the RF treatment handpiece shown in FIG. 9.

As shown in FIGS. 9 and 10, an RF treatment handpiece may comprise a base 901 and a plurality of electrodes 902 (shown in circles in FIG. 9), wherein the plurality of electrodes 902 are mounted on the base 901, and the base 901 has a structural design similar to a conventional design.

The plurality of electrodes 902 are mounted on a bottom side of the base 1, and the plurality of electrodes 902 may comprise a plurality of printed circuit nodes or a plurality of RF electrode microneedles. In cases where the plurality of electrodes 902 comprise a plurality of printed circuit nodes, a printed circuit is applied to connect each of the plurality of electrodes 902 in series, and the device having this design can be used for non-invasive therapies. In cases where the plurality of electrodes 902 comprise a plurality of RF electrode microneedles, wires are applied to connect each of the plurality of electrodes 902 in series, and the device having this design can be used for invasive therapies. The plurality of electrodes 902 are arranged in a dot matrix pattern, and characterized in an M*N matrix, which has M rows and N columns, wherein M and N are integers greater than or equal to 2. In the embodiment shown in FIG. 9, M and N are both equal to 4. Any two adjacent electrodes in each row are equally spaced apart, and any two adjacent electrodes in each column are also equally spaced apart.

Good therapeutic effects can be achieved only if the RF energy field completely covers the target region. Take underarm odor treatment as one example: if the heat target region is 50%, the rest 50% of the treatment region still contains apocrine sweat glands from which body odor is still generated even though its production is reduced. In such case, an ideal cure rate cannot be achieved. In light of this situation, the heat target region must cover the entire treatment area in order to achieve an ideal therapeutic effect. As such, the plurality of electrodes 902 need to be arranged to have a density of 16-100/cm2, and preferably 49/cm2.

As shown in FIG. 9, electrode (i, j) 902 and electrode (i+1, j+1) 902 are series-connected into a branch, where $1 \leq i \leq M-1$ and $1 \leq j \leq N-1$. Electrode (M, 1) 902 and electrode (1, N) 902 in a branch where M and N are odd numbers are parallel-connected with another branch where i is an odd number to form an electrode in the overall circuit. In this embodiment, a cathode is formed. At the same time, electrode (M, 1) 902 and electrode (1, N) 902 in a branch where M and N are even numbers are parallel-connected with another branch where i is an even number to form an opposite electrode in the overall circuit. In this embodiment, an anode is formed.

Figure 11:
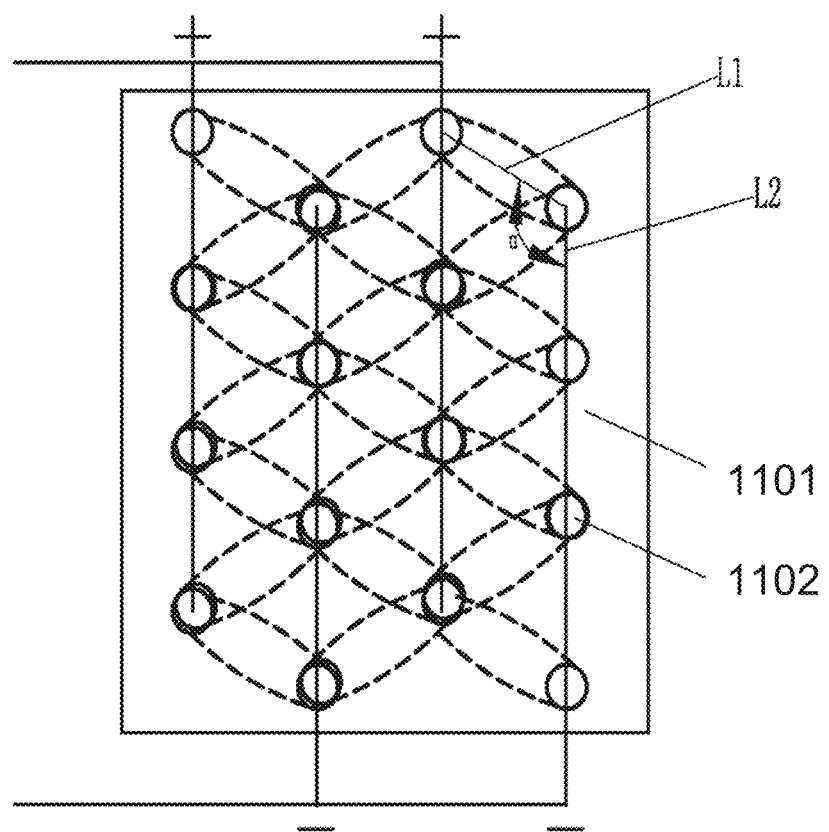
FIG. 11 illustrates a schematic diagram of an RF treatment handpiece according to Embodiment 2 of the present disclosure.

Set the distance between the two electrodes 902 as L, and the heat concentration area covered by two adjacent electrodes 902 as D, illustrated by the dotted line in FIGS. 8, 9, and 11. In this embodiment, the coverage area of the electrodes 902 is 9L2, and the effective heating area is 24D.

As shown in FIG. 10, where the plurality of electrode 1002 employ a plurality of RF electrode microneedles, each of the plurality of RF electrode microneedles takes a cylindrical shape and has a height of 2 mm-5 mm. Each of the plurality of RF electrode microneedles has a tapered tip at a first end far from the base, and has a second end connecting the base 1001, wherein the second end is coated with an insulating layer 1003 having a height of 0.3 mm-2 mm. Additionally, one of the plurality of RF electrode microneedles may be provided with a blind hole, configured to form in a direction from the base-connecting end to the end with the tapered tip, wherein the bottom of the blind hole is close to the tapered tip and is provided with a temperature sensor 1004, configured to connect to the main machine during use.

The main machine may output two modes of RF, a continuous output mode and a pulsed output mode. Under the continuous output mode, target tissues need to maintain a temperature of 60-70° C. for a period of 2-10 s. Under the pulsed output mode, due to the short time period of action, usually 0.1 s-1 s, target tissues require a higher temperature of 70-80° C. for effective heating. Because the RF output mode determines the duration of reaction, the temperature sensor 1004 has a response time of 0.05 s-0.5 s for the continuous output mode, a response time of 0.001 s-0.05 s for the pulsed output mode.

Embodiment 2

Figure 12:
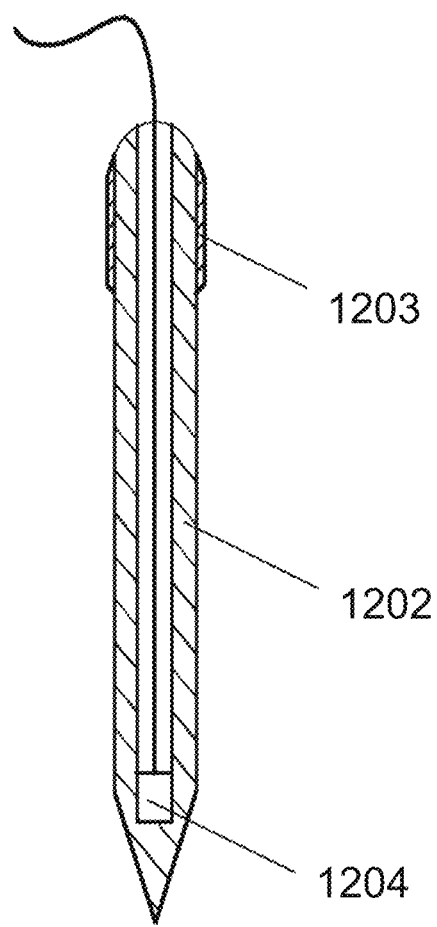
FIG. 12 is a schematic diagram of a RF electrode microneedle employed in the RF treatment handpiece shown in FIG. 11.

As shown in FIGS. 11 and 12, an RF treatment handpiece may comprise a base 1101 and a plurality of electrodes 1102, wherein the plurality of electrodes 1102 are mounted on the base 1101, and the base 1101 has a structural design similar to a conventional design.

The plurality of electrodes 1102 are mounted on a bottom side of the base, and the plurality of electrodes 1102 may comprise a plurality of printed circuit nodes or a plurality of RF electrode microneedles. In cases where the plurality of electrodes 1102 comprise a plurality of printed circuit nodes, a printed circuit is applied to connect each of the plurality of electrodes 1102 in series, and the device having this design can be used for non-invasive therapies. In cases where the plurality of electrodes 1102 comprise a plurality of RF electrode microneedles, wires are applied to connect each of the plurality of electrodes 1102 in series, and the device having this design can be used for invasive therapies. The plurality of electrodes 1102 are arranged in a dot matrix pattern, characterized by an M*N matrix, which has M rows and N columns, where M and N are integers greater than or equal to 2. In the embodiment shown in FIG. 11, M and N are both equal to 4. Any two adjacent electrodes in each column are equally spaced apart.

In the embodiment shown in FIG. 11, the electrodes 1102 in at least one row or in at least one column are on a curved line if connected; all electrodes 1102 in each of the columns form a straight line whereas all electrodes in each of the rows are not in a straight line. Set the connecting line between any particular electrode 1102 and one of its adjacent anode-role electrode 1102 as L1, the connecting line between the same electrode 1102 and one of its adjacent cathode-role electrode 1102 as L2, and the angle formed between L1 and L2 as a, where a is 60° or 120°.

All of the electrodes 1102 of each column are series-connected to form a branch. Among the series branches, the branches of odd-number columns are connected in parallel to form one electrode, or anode in this embodiment, in the overall circuit, whereas the branches of even-number columns are connected in parallel to form the opposite electrode, or cathode in this embodiment. Specifically in this embodiment, the coverage area of the electrodes 1102 is 7.8L2, and the effective heating area is 21D.

As shown in FIG. 12, where the plurality of electrode 1202 employ a plurality of RF electrode microneedles, each of the plurality of RF electrode microneedles takes a cylindrical shape and has a height of 2 mm-5 mm. Each of the plurality of RF electrode microneedles has a tapered tip at a first end far from the base, and has a second end connecting the base 1201, wherein the second end is coated with an insulating layer 1203 having a height of 0.3 mm-2 mm. Additionally, one of the plurality of RF electrode microneedles may be provided with a blind hole, configured to form in a direction from the base-connecting end to the end with the tapered tip, wherein the bottom of the blind hole is close to the tapered tip and is provided with a temperature sensor 1204, configured to connect to the main machine during use.

The conventional RF treatment handpiece shown in FIG. 8 has 12 high-energy concentration regions, whereas Embodiment 1 of the RF treatment handpiece as disclosed herein has 24 high energy concentration regions, and Embodiment 2 has 21 high energy concentration regions. The three configurations as illustrated in FIGS. 8, 9 and 11 have heat concentration regions per unit area of 1.33D/L2, 2.67D/L2 and 2.69D/L2, respectively. Thus Embodiment 2 has more uniform and more sufficient heating, and Embodiment 1 has a slightly lower heat concentration density than Embodiment 2.

Furthermore, for invasive treatment, the three configurations as illustrated in FIGS. 8, 9 and 11 all have 16 minimally invasive regions, and have 9L2, 9L2 and 7.8L2 respectively. Thus the configuration as shown in FIG. 11 has the smallest area for invasive treatment.

Existing microneedle therapies are achieved by pushing microneedles into the skin tissues by motors, and in this process microneedles subject to reaction forces before piercing into the skin and subject to resistance forces after piecing into skin tissues. Since microneedles are somewhat small and take a cylindrical shape, the resistance mainly comes from the reaction force before piercing into the skin. At certain parts of the body, difficulties exist for the microneedles to move, making treatment somewhat hard.

Figure 13:
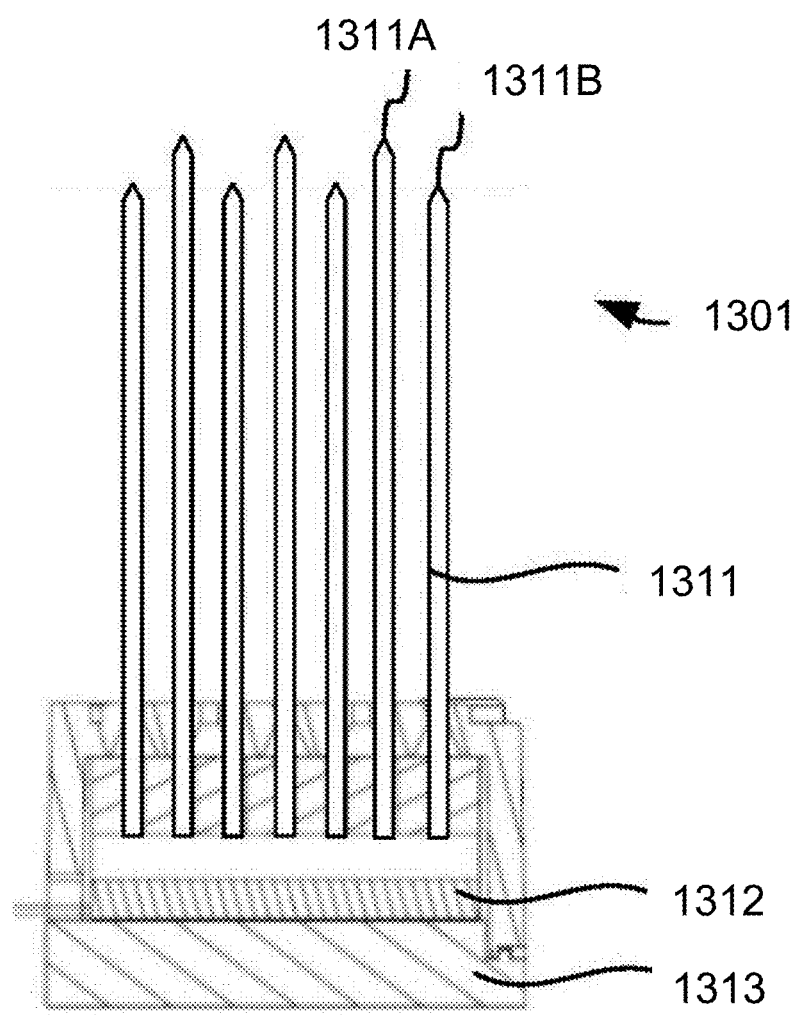
FIG. 13 illustrates the schematic structural diagram of a microneedle member according to one embodiment of the invention.

In view of the issues associated with conventional technologies, this disclosure provides a new type of microneedle member to reduce the difficulties of operation. FIG. 13 illustrates the schematic structural diagram of a microneedle member 1301 according to some embodiment of this disclosure, which comprises a plurality of microneedles 1311, a printed circuit board (PCB) 1312 and a substrate plate 1313, wherein the PCB 1312 is mounted on the substrate plate 1313, and the plurality of microneedles 1311 are mounted on the PCB and are connected with a printed circuit on the PCB 1312 to form RF electrodes, wherein the plurality of microneedles comprise a plurality of long microneedles 1311A and a plurality of short microneedles 1311B, and the plurality of long microneedles 1311A and the plurality of short microneedles 1311B are arranged in an array.

The microneedle member 1301 as disclosed above can effectively reduce the area for the plurality of microneedles 1311 to touch skin, bringing about more ease for the plurality of microneedles 1311 to penetrate into skin under the same driving force of the motor, which solves the issues of difficulties for microneedle penetration.

In the embodiment, the plurality of long microneedles 1311A and the plurality of short microneedles 1311B are both mounted on the bottom base of the plurality of microneedles. Preferably, the length of the plurality of long microneedles 1311A is 0.1 mm-5.0 mm longer than that of the plurality of short microneedles 1311B. The term length herein refers to the length of the portion of the plurality of microneedles outside the bottom base.

Figure 14:
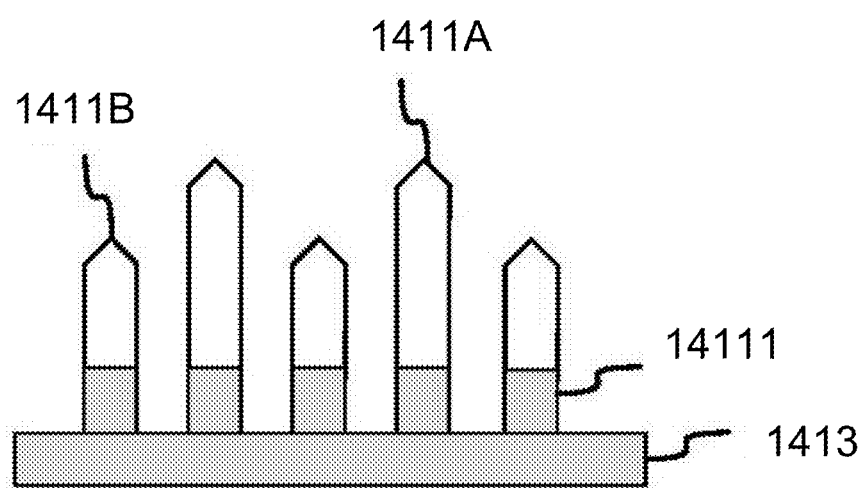
FIG. 14 illustrates a side view of the schematic diagram of a microneedle member according to another embodiment of this invention.

In another embodiment as shown in FIG. 14, a side view of the schematic diagram of a microneedle member is illustrated, wherein a bottom end of each of the plurality of long microneedles 1411A and each of the plurality of short microneedles 1411B is coated with an insulating layer 14111 in order to prevent the bottom portion of the microneedles from discharging and in turn to provide protection to the epidermis layer and dermis layer. The height of the insulating layer 14111 can be varied depending on different clinical needs. For example, the height of the insulating layer 14111 can be 0.1 mm-0.5 mm, or preferably 0.3 mm, for the treatment of stretch marks without hurting the epidermis, and 1.0 mm-2.5 mm, or preferably 1.8 mm, for the treatment of hyperhidrosis, which selectively and directly targets the apocrine sweat glands under skin and can effectively avoid the thermal damage to epidermis and dermis.

Figure 15:
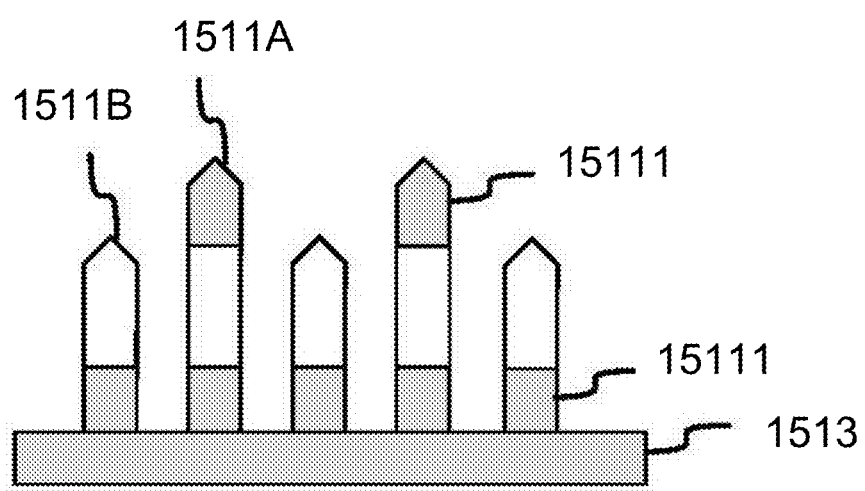
FIG. 15 illustrates a side view of the schematic diagram of a microneedle member according to yet another embodiment of this invention.

In yet another embodiment as shown in FIG. 15, a side view of the schematic diagram of a microneedle member is illustrated, wherein besides the coating of an insulating layer on the bottom end of each of the plurality of long microneedles 1511A and each of the plurality of short microneedles 1511B, a top end of each of the plurality of long microneedles 1511A is also coated with a second insulating layer to prevent this portion of the microneedles from discharging. Compared with the embodiment shown in FIG. 14, this embodiment of the microneedle member shown in FIG. 15, wherein the top ends of the plurality of long microneedles 1511A undergo this special treatment, has an advantage of a more even heat distribution in the heating region.

Figure 16:
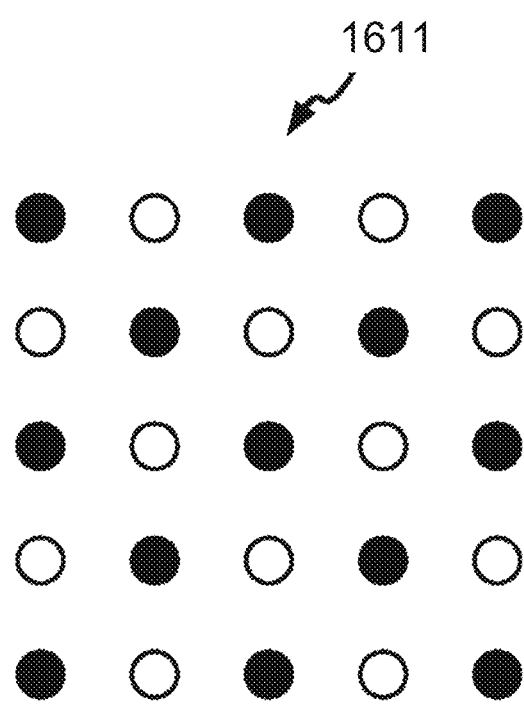
FIG. 16 illustrates a schematic diagram of the arrangement of the plurality of microneedles on the substrate according to one embodiment of the invention.

In yet another embodiment as shown in FIG. 16, a schematic diagram of the arrangement of the microneedles on the substrate plate is illustrated, wherein the plurality of microneedles 1611 are arranged in an array on the substrate plate. As shown in the figure, microneedles of same lengths are illustrated in the same color. For example, the plurality of long microneedles can be illustrated in black and the plurality of short microneedles in gray, and vice versa.

In general, the array of the microneedles are arranged in an M*N matrix, wherein M and N are horizontal and vertical coordinates respectively. The microneedle at the bottom left corner has a coordinate of (0,0), and other microneedles can be (i, j), where $0 \leq i \leq M$ and $0 \leq j \leq N$. The microneedles where i+j gives an even number are of a first same standard and the microneedles where i+j gives an odd number are of a second same standard. For example, the microneedles where i+j gives an even number are all long microneedles, and the microneedles where i+j gives an odd number are all short microneedles, and vice versa.

Preferably, the plurality of long microneedles constitute one electrode of the RF electrodes whereas the plurality of short microneedles constitute the opposite electrode. For example, the plurality of long microneedles may be anode, and the plurality of short microneedles may be cathode.

Figure 17:
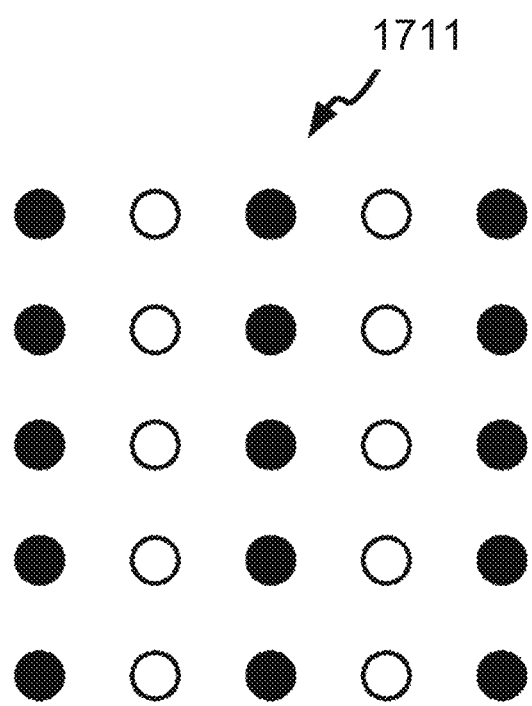
FIG. 17 illustrates a schematic diagram of the arrangement of the plurality of microneedles on the substrate plate according to another embodiment of the invention.

FIG. 17 illustrates a schematic diagram of the arrangement of the microneedle member according to some embodiment of the invention, wherein microneedles of the same color have the same length. The array of the microneedles are arranged in an M*N matrix, wherein M and N are horizontal and vertical coordinates respectively. The microneedle at the bottom left corner has a coordinate of (0, 0), and other microneedles can be (i, j), where $0 \leq i \leq M$ and $0 \leq j \leq N$. The microneedles on the same row or on the same column have the same length. For example, the microneedles on row i, where i is an even number, are of a first same length, whereas the microneedles on row i, where i is an odd number, are of a second same length.

Figure 18A:
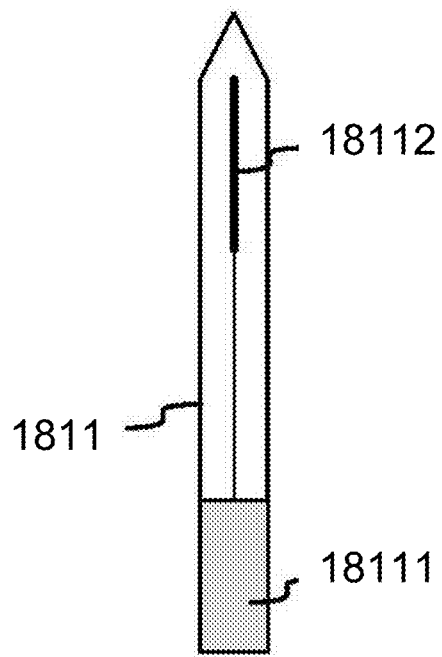
FIG. 18A illustrates a schematic structural diagram of a microneedle according to another embodiment.
Figure 18B:
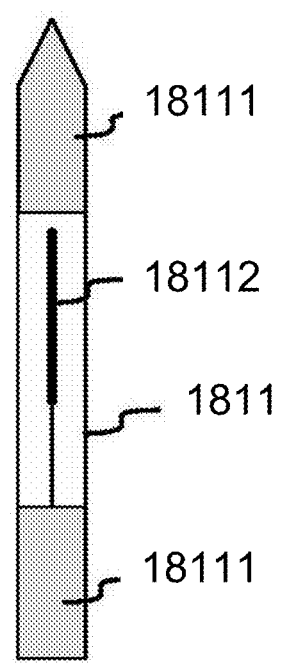
FIG. 18B is a schematic structural diagram of the microneedle in another configuration.

FIGS. 18A and 18B illustrates schematic structural diagrams of a microneedle 1811 according to yet another embodiment, wherein the microneedle further comprises a temperature sensor 18112, disposed inside the microneedle, which is on top of the microneedle structure as shown in FIG. 14 or FIG. 15. Insulating layer 18111 can be disposed at the bottom portion of the microneedle 1811 in the embodiment of FIG. 18A, and at both the bottom and the head portions of the microneedle 1811 in the embodiment of FIG. 18B.

Therapies using RF microneedles are mechanistically based on thermal effects, which in turn induce denaturing of collagens for skin rejuvenation, decompose cells in sebaceous glands for acne treatment, and decompose cells in apocrine sweat glands for hyperhidrosis treatment, etc. The temperature sensor 18112 arranged inside a microneedle can be used for monitoring the temperatures in the target tissues, and for example, the temperature sensor 18112 can be a resistance temperature sensor 18112. Due to the relative even energy distribution within the microneedle array, the temperature sensor 18112 can be arranged in only one microneedle, but not in others. The temperature sensor 18112 can be arranged inside the discharge microneedle, or more specifically, can be arranged inside the discharge portion of the microneedle, as illustrated in FIG. 18.

In some embodiment, the temperature sensor 18112 has a response time of 10 ms-200 ms, which can be, for example, 100 ms.

Figure 19:
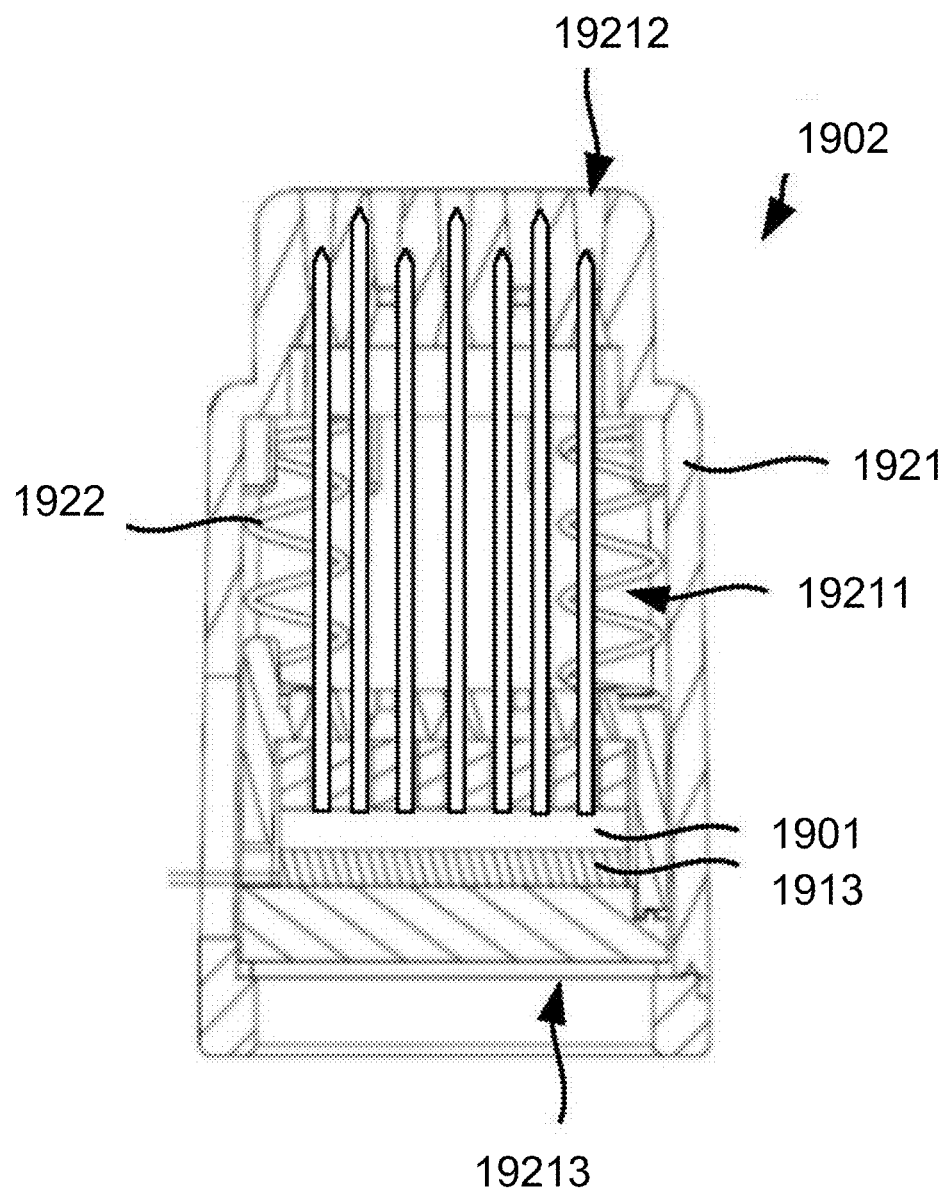
FIG. 19 illustrates a schematic structural diagram of an RF microneedle treatment unit according to one embodiment of the invention.

FIG. 19 illustrates a schematic structural diagram of an RF microneedle treatment unit according to some embodiment of the invention. The RF microneedle treatment unit 1902 comprises a housing 1921 and a motor (not shown), wherein the housing 1921 is provided with a cavity 19211, a front end of the housing 1921 is provided with a plurality of microneedle through-holes 19212 which connect the cavity 19211, a rear end of the housing 1902 is provided with a plurality of microneedle bullet-holes 19213. The RF microneedle treatment unit 1902 also comprises the microneedle member 1901 as disclosed above, wherein the microneedle member 1901 is fittingly arranged between the plurality of microneedle through-holes 19212 and the plurality of microneedle bullet-holes 19213 through an elastic member 1922, and the plurality of microneedles 1911 in the microneedle member 1901 are configured to be pushed by a driving rod of the motor to move out of the plurality of microneedle through-holes 19212 through the plurality of microneedle bullet-holes 19213.

The working mechanism of the RF microneedle treatment unit 1902 is as follows. The driving rod of the motor pushes the microneedle member 1901 forward through the plurality of microneedle bullet-holes 19213, and the plurality of microneedles move outside through the plurality of microneedle through-holes 19212 to penetrate the skin for treatment. Then the driving rod of the motor withdraws and the elastic member 1922 in the RF microneedle treatment unit, for example, a spring, moves the plurality of microneedles backward, causing the plurality of microneedles to withdraw from inside the skin tissues to inside the cavity 19211 of the RF microneedle treatment unit.

In summary, by modifying the conventional microneedle member to comprise both a plurality of long microneedles and a plurality of short microneedles without changing other existing components, the invention conveniently overcomes the difficulties for microneedles to reach target regions, and achieves greater therapeutic effects through further improvements on the plurality of long microneedles and the plurality of short microneedles. This invention effectively solves the weaknesses of conventional technologies and thus has high commercial values.

Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A radio frequency (RF) treatment apparatus, comprising a main machine and a treatment handpiece, wherein:
the main machine comprises a power supply disposed therein and is coupled to the treatment handpiece via a cable;
the treatment handpiece comprises an RF output device, the RF output device comprising a plurality of RF electrodes;
in the treatment handpiece, the plurality of RF electrodes are mounted on a bottom side of a base and comprise a plurality of printed circuit nodes or a plurality of RF electrode microneedles;
the plurality of RF electrodes are arranged in a dot matrix pattern;
the plurality of RF electrodes are arranged in an M×N matrix, where M and N represent a number of rows and a number of columns respectively and are integers ≥2;
electrode (i, j) and electrode (i+1, j+1) are series-connected into a branch, wherein 1≤i≤M−1 and 1≤j≤N−1;
electrode (M, 1) and electrode (1, N) in a first branch where a portion of the M×N matrix that are of odd numbers are parallel-connected with a second branch where i is an odd number to form an electrode in an overall circuit; and
electrode (M, 1) and electrode (1, N) in a third branch where a portion of the M×N matrix that are of even numbers are parallel-connected with a fourth branch where i is an even number to form an opposite electrode in the overall circuit;
wherein the M×N matrix is configured to improve current distribution uniformity suitable for stimulating regeneration of collagen and promoting tightening of fibrous tissues.

2. The RF treatment apparatus according to claim 1, wherein in the treatment handpiece, any two adjacent electrodes among the plurality of RF electrodes in each row of the M×N matrix are equally spaced apart, and any two adjacent electrodes in each column of the M×N matrix are equally spaced apart.

3. The RF treatment apparatus according to claim 1, further comprising a temperature sensor configured sense a temperature of a target region, wherein the target region is controlled to have a temperature of 40-50° C. in a continuous treatment mode, wherein the continuous treatment mode has a treatment period of 1-10 s.

4. The RF treatment apparatus according to claim 1, wherein: the plurality of RF electrodes comprise a plurality of RF electrode microneedles including a plurality of long microneedles forming one of an anode or a cathode of the plurality of RF electrodes, and a plurality of short microneedles forming another one of the anode or the cathode of the plurality of RF electrodes; the plurality of long microneedles have a length 0.1-5.0 mm longer than a length of the plurality of short microneedles; a bottom end of each of the plurality of long microneedles and each of the plurality of short microneedles are coated with an insulating layer, the insulating layer has a height of 0.1-2.5 mm, and a top end of each of the plurality of long microneedles is further coated with a second insulating layer.

5. The RF treatment apparatus according to claim 4, further comprising: an automatic impedance matching device configured to detect skin impedance and control needed power density to ensure a preset power is output to different patients and on different skin regions under therapy; and a control console configured to set an alert temperature level to the target region temperature.

6. A radio frequency (RF) treatment apparatus, comprising a main machine and a treatment handpiece, wherein:
the main machine comprises a power supply disposed therein and is coupled to the treatment handpiece via a cable;
the treatment handpiece comprises an RF output device, the RF output device comprising a plurality of RF electrodes;
in the treatment handpiece, the plurality of RF electrodes are mounted on a bottom side of a base and comprise a plurality of printed circuit nodes or a plurality of RF electrode microneedles;
the plurality of RF electrodes are arranged in a dot matrix pattern, wherein:
the plurality of electrodes are arranged in an M×N matrix, where M and N represent a number of rows and a number of columns respectively and are integers ≥2;
among the plurality of RF electrodes all electrodes in at least one row, or in at least one column, of the M×N matrix are on a curved line;
among the plurality of RF electrodes all electrodes in each column of the M×N matrix are series-connected to form a branch, wherein:
branches formed at odd-number columns are connected in parallel to form an electrode in an overall circuit; and
branches formed at even-number columns are connected in parallel to form an opposite electrode in the overall circuit;
wherein the M×N matrix is configured to improve current distribution uniformity suitable for stimulating regeneration of collagen and promoting tightening of fibrous tissues.

7. The RF treatment apparatus according to claim 6, wherein among the plurality of RF electrodes all electrodes in each of the columns are on a straight line, and among the plurality of RF electrodes all electrodes in each of the rows are not on a straight line.

8. The RF treatment apparatus according to claim 7, wherein an angle formed between a first connecting line, connected between one of the plurality of RF electrodes and one of an anode-role electrode adjacent thereto, and a second connecting line, connected between the one of the plurality of RF electrodes and one of a cathode-role electrode adjacent thereto is 60° or 120°.

9. The RF treatment apparatus according to claim 6, further comprising a temperature sensor configured sense a temperature of a target region, wherein the target region is controlled to have a temperature of 40-50° C. in a continuous treatment mode.

10. The RF treatment apparatus according to claim 9, wherein the RF output device has an output frequency of 0.3 MHz-100 MHz.

11. The RF treatment apparatus according to claim 9, wherein the continuous treatment mode has a treatment period of 1-10 s.

12. The RF treatment apparatus according to claim 6, further comprising a temperature sensor configured sense a temperature of a target region, wherein the target region is controlled to have a temperature of 60-70° C. in a pulsed treatment mode.

13. The RF treatment apparatus according to claim 12, wherein the RF output device has an output frequency of 0.3 MHz-100 MHz.

14. The RF treatment apparatus according to claim 12, wherein the pulsed treatment mode has a treatment period of 0.1-0.5 s.

15. The RF treatment apparatus according to claim 14, wherein the temperature sensor has a response time of 10-200 ms.

16. The RF treatment apparatus according to claim 15, wherein the temperature sensor has a response time of 100 ms.

17. The RF treatment apparatus according to claim 6, wherein the plurality of RF electrodes comprise a plurality of RF electrode microneedles including a plurality of long microneedles forming one of an anode or a cathode of the plurality of RF electrodes, and a plurality of short microneedles forming another one of the anode or the cathode of the plurality of RF electrodes, wherein the plurality of long microneedles have a length 0.1-5.0 mm longer than a length of the plurality of short microneedles.

18. The RF treatment apparatus according to claim 17, wherein a bottom end of each of the plurality of long microneedles and each of the plurality of short microneedles are coated with an insulating layer.

19. The RF treatment apparatus according to claim 18, wherein the insulating layer has a height of 0.1-2.5 mm, and a top end of each of the plurality of long microneedles is further coated with a second insulating layer.

20. The RF treatment apparatus according to claim 17, further comprising an automatic impedance matching device configured to detect skin impedance and control needed power density to ensure a preset power is output to different patients and on different skin regions under therapy.

* * * * *